US012697203B2

(12) United States Patent
Rasmussen et al.

(10) Patent No.: US 12,697,203 B2
(45) Date of Patent: Aug. 4, 2026

(54) STENT GRAFT ASSEMBLY

(71) Applicant: Cook Medical Technologies LLC, Bloomington, IN (US)

(72) Inventors: Erik E. Rasmussen, Slagelse (DK); Bent Oehlenschlaeger, Solroed Strand (DK); Jarin Kratzberg, Lafayette, IN (US); Robert Binskin, Queensland (AU); Chantelle King, Queensland (AU)

(73) Assignee: Cook Medical Technologies LLC, Bloomington, IN (US)

( * ) Notice: Subject to any disclaimer, the term of this patent is extended or adjusted under 35 U.S.C. 154(b) by 450 days.

(21) Appl. No.: 18/380,413

(22) Filed: Oct. 16, 2023

(65) Prior Publication Data

US 2024/0122695 A1 Apr. 18, 2024

(30) Foreign Application Priority Data

Oct. 17, 2022 (GB) ...................................... 2215295
Oct. 17, 2022 (GB) ...................................... 2215296
(Continued)

(51) Int. Cl.
*A61F 2/07* (2013.01)
*A61F 2/954* (2013.01)
(Continued)

(52) U.S. Cl.
CPC ................ *A61F 2/07* (2013.01); *A61F 2/954* (2013.01); *A61F 2/89* (2013.01);
(Continued)

(58) Field of Classification Search
CPC ......... A61F 22/07–2002/075; A61F 250/0037; A61F 2002/91508; A61F 2230/0023
See application file for complete search history.

(56) References Cited

U.S. PATENT DOCUMENTS 9,198,786 B2 12/2015 Moore et al.
9,427,307 B2 8/2016 Pearson et al.
(Continued)

FOREIGN PATENT DOCUMENTS

AU 2010202544 B1 8/2010
AU 2016256777 B1 4/2017
(Continued)

OTHER PUBLICATIONS

European Search Report, Application No. 23275148.7, dated May 20, 2025.
(Continued)

*Primary Examiner* — Rebecca S Preston
(74) *Attorney, Agent, or Firm* — MacMillan, Sobanski & Todd, LLC

(57) ABSTRACT

A stent graft for deployment in the aortic arch including at least a proximal stent ring at the proximal end of the tubular graft material, at least one fenestration provided in a side wall of the tubular graft material, an internal branch disposed within the lumen of the stent graft and extending from the fenestration. A fenestration-supporting stent ring supports the fenestration between two struts and an apex of the fenestration supporting ring. The proximal stent ring has plurality of stent units including at least one scallop unit, at least one supporting unit, and at least one body unit. The proximal apex of each scallop unit is located at a laterally extending edge of the scallop in a first circumferential region and the proximal apex of each supporting unit is located a second circumferential region. The first and second struts of each of the at least one scallop unit are shorter than the first and second struts of each of the at least one supporting unit.

20 Claims, 13 Drawing Sheets

(30) Foreign Application Priority Data

| | | |
|---|---|---|
| Oct. 17, 2022 | (GB) | .................................... 2215297 |
| Oct. 17, 2022 | (GB) | .................................... 2215299 |

(51) Int. Cl.

| | |
|---|---|
| *A61F 2/89* | (2013.01) |
| *A61F 2/915* | (2013.01) |

(52) U.S. Cl.

CPC ............... *A61F 2002/91508* (2013.01); *A61F 2210/0014* (2013.01); *A61F 2220/0075* (2013.01); *A61F 2230/0023* (2013.01); *A61F 2230/0067* (2013.01); *A61F 2250/0037* (2013.01); *A61F 2250/006* (2013.01); *A61F 2250/0098* (2013.01)

(56) References Cited

U.S. PATENT DOCUMENTS

| | | | |
|---|---|---|---|
| 9,629,734 | B2 | 4/2017 | Ma et al. |
| 9,662,196 | B2 | 5/2017 | Roeder et al. |
| 9,737,384 | B2 | 8/2017 | Coghlan et al. |
| 10,098,767 | B2 | 10/2018 | Maggard et al. |
| 10,779,930 | B2 | 9/2020 | Roeder et al. |
| 2004/0230287 | A1* | 11/2004 | Hartley ................... A61F 2/954 606/108 |
| 2006/0136046 | A1* | 6/2006 | Hartley ..................... A61F 2/07 623/1.35 |
| 2006/0247761 | A1 | 11/2006 | Greenberg et al. |
| 2007/0233229 | A1 | 10/2007 | Berra et al. |
| 2009/0043377 | A1 | 2/2009 | Greenberg et al. |
| 2010/0249899 | A1 | 9/2010 | Chuter et al. |
| 2013/0289702 | A1* | 10/2013 | Coghlan ................... A61F 2/07 623/1.13 |
| 2013/0289703 | A1 | 10/2013 | Kinkade et al. |
| 2016/0106564 | A1* | 4/2016 | Roeder ................... A61F 2/064 623/1.13 |
| 2016/0120667 | A1 | 5/2016 | Bolduc et al. |
| 2016/0193029 | A1 | 7/2016 | Shalev |
| 2018/0021155 | A1 | 1/2018 | Hadley et al. |
| 2018/0036110 | A1 | 2/2018 | King et al. |
| 2018/0042739 | A1 | 2/2018 | Hagaman et al. |
| 2018/0228593 | A1 | 8/2018 | Eaton et al. |
| 2018/0228594 | A1 | 8/2018 | Skender et al. |
| 2018/0303641 | A1 | 10/2018 | Roeder et al. |
| 2020/0146807 | A1 | 5/2020 | Kratzberg et al. |
| 2020/0330215 | A1 | 10/2020 | Xiao et al. |
| 2021/0015643 | A1 | 1/2021 | Brocker et al. |
| 2021/0052364 | A1 | 2/2021 | Guo et al. |

FOREIGN PATENT DOCUMENTS

| | | | |
|---|---|---|---|
| EP | 1 472 990 | A1 | 11/2004 |
| EP | 2 079 397 | B1 | 3/2010 |
| EP | 2 471 498 | A1 | 7/2012 |
| EP | 2 749 252 | A1 | 7/2014 |
| EP | 3017790 | A2 | 5/2016 |
| EP | 3 378 438 | A1 | 9/2018 |
| EP | 3395295 | A1 | 10/2018 |
| EP | 3 449 871 | A2 | 3/2019 |
| EP | 3 646 817 | A2 | 5/2020 |
| EP | 3 943 046 | A1 | 1/2022 |
| EP | 4 026 518 | A1 | 7/2022 |
| WO | WO 2005/023149 | A2 | 3/2005 |
| WO | 2 081 515 | A0 | 5/2008 |
| WO | WO 2008/057568 | A1 | 5/2008 |
| WO | WO 2009/082444 | A1 | 7/2009 |
| WO | WO 2010/111583 | A1 | 9/2010 |
| WO | WO 2013/074990 | A1 | 5/2013 |
| WO | WO 2014/188412 | A2 | 11/2014 |
| WO | WO 2015/081175 | A1 | 6/2015 |
| WO | WO 2020/074598 | A1 | 4/2020 |
| WO | WO 2020/236834 | A1 | 11/2020 |

OTHER PUBLICATIONS

Japanese Office Action, Application No. 2023-178663, dated Jun. 24, 2025.

Great Britain Combined Search and Examination Report under Sections 17 and 18(3), Application No. GB2404409.1, dated Apr. 16, 2024.

Great Britain Examination Report under Section 18(3), Application No. GB2404409.1, dated Jan. 16, 2025.

Japanese Office Action, Application No. 2023178663, dated Jan. 8, 2025.

GB Combined Search and Examination Report issued Mar. 28, 2023 in GB Application No. 2215296.1.

Zeng et al., "Application of Physician-Modified Fenestrated Stent Graft in Urgent Endovascular Repair of Abdominal Aortic Aneurysm with Hostile Neck Anatomy", (2016) Medicine 95:46, e5455, pp. 1-6.

* cited by examiner

STENT GRAFT ASSEMBLY

RELATED APPLICATIONS

This application claims the benefit of United Kingdom patent applications GB2215296.1 filed Oct. 17, 2022, GB2215297.9 filed Oct. 17, 2022, GB2215299.5 filed Oct. 17, 2022, and GB2215295.3 filed Oct. 17, 2022, the contents of which are incorporated by reference in their entireties.

FIELD OF THE INVENTION

The present invention relates to an endoluminally implantable medical device and a method of use thereof. The endoluminally implantable medical device may be for insertion into the vasculature of a human.

BACKGROUND

Endoluminal prostheses, such as stents and stent-grafts, may be used for treating damaged or diseased vessels in the body of a human. For example, a stent-graft may be used for repairing an aneurysm in the thoracic or abdominal aorta. Such a stent-graft is placed inside the vessel and provides some or all of the functionality of the original, healthy vessel.

One of the challenges of designing and using an endoluminal prosthesis is providing sufficient sealing of the prosthesis against the wall of the vessel. Where a prosthesis is deployed in a blood vessel, if the seal is insufficient it can result in leakage of blood flow between the prosthesis and the vessel wall—commonly referred to as an endoleak—which can impair treatment of the patient as the aneurysm may not be depressurised and may grow.

Achieving sufficient sealing of a prosthesis is made more challenging where the vessel has a high degree of curvature. Achieving sufficient sealing of a prosthesis is also made more challenging where the area of healthy tissue available for the prosthesis to seal against—also known as the landing zone—is limited. For example, where the region for repair is located adjacent, or even between, branches of the vessel the landing zone may be severely limited.

A particularly challenging region for treatment has been found to be the aortic arch. In practice, there is difficulty in designing and deploying a prosthesis that can accommodate the challenging topology of the aortic arch.

SUMMARY

The present invention seeks to provide an improved endoluminally implantable medical device and method. Disclosed and described is a stent graft for deployment in the aortic arch including a plurality of expandable stent rings arranged along a length of tubular graft material having a proximal end and a distal end, the plurality including at least a proximal stent ring at the proximal end of the tubular graft material and a distal stent ring at or near the distal end of the tubular graft material, and at least one intermediate stent ring between the proximal stent ring and the distal stent ring; at least one fenestration provided in a side wall of the tubular graft material; an internal branch disposed within the lumen and extending from the fenestration toward an end of the stent graft; first and second circumferential regions at the proximal end of the graft; a scallop in the first circumferential region and longitudinally aligned with the fenestration; wherein the at least one intermediate stent ring is a fenestration-supporting stent ring, wherein the fenestration-supporting stent ring is a zig-zag stent having a plurality of proximal apices and a plurality of distal apices, the proximal and distal apices connected to each other by a plurality of stent struts extending therebetween, wherein at least one of the distal apices is a fenestration-supporting apex; wherein at least one fenestration is provided between two struts of the fenestration-supporting stent ring, the combination of two struts and the fenestration-supporting apex of the fenestration-supporting stent ring defining two sides and the distal end of the fenestration; and wherein the fenestration has a proximal edge, the proximal edge including at least a portion that is substantially perpendicular to the longitudinal axis of the stent graft; wherein the proximal stent ring comprises a plurality of stent units, each stent unit comprising first and second struts connected by a proximal apex, the stent ring comprising a plurality of distal apices, each stent unit being connected to a neighboring stent unit by a distal apex; wherein the plurality of stent units includes at least one scallop unit and at least one supporting unit, where the proximal apex of each scallop unit is located at a laterally extending edge of the scallop in the first circumferential region and the proximal apex of each supporting unit is located in the second circumferential region; and wherein the first and second struts of each of the at least one scallop unit are shorter than the first and second struts of each of the at least one supporting unit.

A stent graft for deployment in the aortic arch including a plurality of expandable stent rings arranged along a length of tubular graft material having a proximal end and a distal end, the plurality including at least a proximal stent ring at the proximal end of the tubular graft material and a distal stent ring at or near the distal end of the tubular graft material, and at least one intermediate stent ring between the proximal stent ring and the distal stent ring; at least one fenestration provided in a side wall of the tubular graft material; an internal branch disposed within the lumen and extending from the fenestration toward an end of the stent graft; first and second circumferential regions at the proximal end of the graft material; a scallop in the first circumferential region and longitudinally aligned with the fenestration; wherein the at least one intermediate stent ring is a fenestration-supporting stent ring, wherein the fenestration-supporting stent ring is a zig-zag stent having a plurality of proximal apices and a plurality of distal apices, the proximal and distal apices connected to each other by a plurality of stent struts extending therebetween, wherein at least one of the distal apices is a fenestration-supporting apex; wherein at least one fenestration is provided between two struts of the fenestration-supporting stent ring, the combination of two struts and the fenestration-supporting apex of the fenestration-supporting stent ring defining two sides and the distal end of the fenestration; wherein the fenestration has a proximal edge, the proximal edge including at least a portion that is substantially perpendicular to the longitudinal axis of the stent graft; wherein the proximal stent ring comprises a plurality of stent units, each stent unit comprising first and second struts connected by a proximal apex, the stent ring comprising a plurality of distal apices, each stent unit being connected to a neighboring stent unit by a distal apex; wherein the plurality of stent units includes a plurality of scallop units each having a proximal apex, a plurality of supporting units each having a proximal apex, and a plurality of body units each having a proximal apex, wherein the proximal apex of each scallop unit is located at a laterally extending edge of the scallop in the first circumferential region, the proximal apex of each supporting unit is located in the second circumferential region, and the proximal apex of each body unit is located in the second circumferential region; wherein the proximal apices of each scallop unit do not extend proximally of the graft material of the scallop; wherein the first and second struts of each scallop unit are shorter than the first and second struts of each supporting unit.

A stent graft for deployment in the aortic arch including a plurality of expandable stent rings arranged along a length of tubular graft material having a proximal end and a distal end, the plurality including at least a proximal stent ring at the proximal end of the tubular graft material and a distal stent ring at or near the distal end of the tubular graft material, and at least one intermediate stent ring between the proximal stent ring and the distal stent ring; at least one fenestration provided in a side wall of the tubular graft material; an internal branch disposed within the lumen and extending from the fenestration toward an end of the stent graft; first and second circumferential regions at the proximal end of the graft material; a scallop in the first circumferential region and longitudinally aligned with the fenestration; at least one conformance tie disposed at least partially circumferentially about a distal end of the proximal stent ring and configured to constrict a diameter of the proximal stent ring; wherein the at least one intermediate stent ring is a fenestration-supporting stent ring, wherein the fenestration-supporting stent ring is a zig-zag stent having a plurality of proximal apices and a plurality of distal apices, the proximal and distal apices connected to each other by a plurality of stent struts extending therebetween, wherein at least one of the distal apices is a fenestration-supporting apex; wherein at least one fenestration is provided between two struts of the fenestration-supporting stent ring, the combination of two struts and the fenestration-supporting apex of the fenestration-supporting stent ring defining two sides and the distal end of the fenestration; wherein the fenestration has a proximal edge, the proximal edge including at least a portion that is substantially perpendicular to the longitudinal axis of the stent graft; wherein the proximal stent ring comprises a plurality of stent units, each stent unit comprising first and second struts connected by a proximal apex, the stent ring comprising a plurality of distal apices, each stent unit being connected to a neighboring stent unit by a distal apex; wherein the plurality of stent units includes a plurality of scallop units each having a proximal apex, a plurality of supporting units each having a proximal apex, and a plurality of body units each having a proximal apex, wherein the proximal apex of each scallop unit is located at a laterally extending edge of the scallop in the first circumferential region, the proximal apex of each supporting unit is located in the second circumferential region, and the proximal apex of each body unit is located in the second circumferential region; wherein the proximal apices of each scallop unit do not extend proximally of the graft material of the scallop; wherein the first and second struts of each scallop unit are shorter than the first and second struts of each supporting unit.

BRIEF DESCRIPTION OF THE DRAWINGS

The invention can be better understood with reference to the following drawings and description. The components are not necessarily to scale, unless specifically identified to be, emphasis instead being placed upon illustrating the principles of the invention. Moreover, in the figures, like reference numerals designate corresponding parts throughout the different views.

FIG. 3 is a schematic diagram showing a profile view of the prosthesis of FIG. 1;

FIGS. 11 and 12 show front and profile views of the prosthesis as shown in FIG. 10;

DETAILED DESCRIPTION

Figure 1:
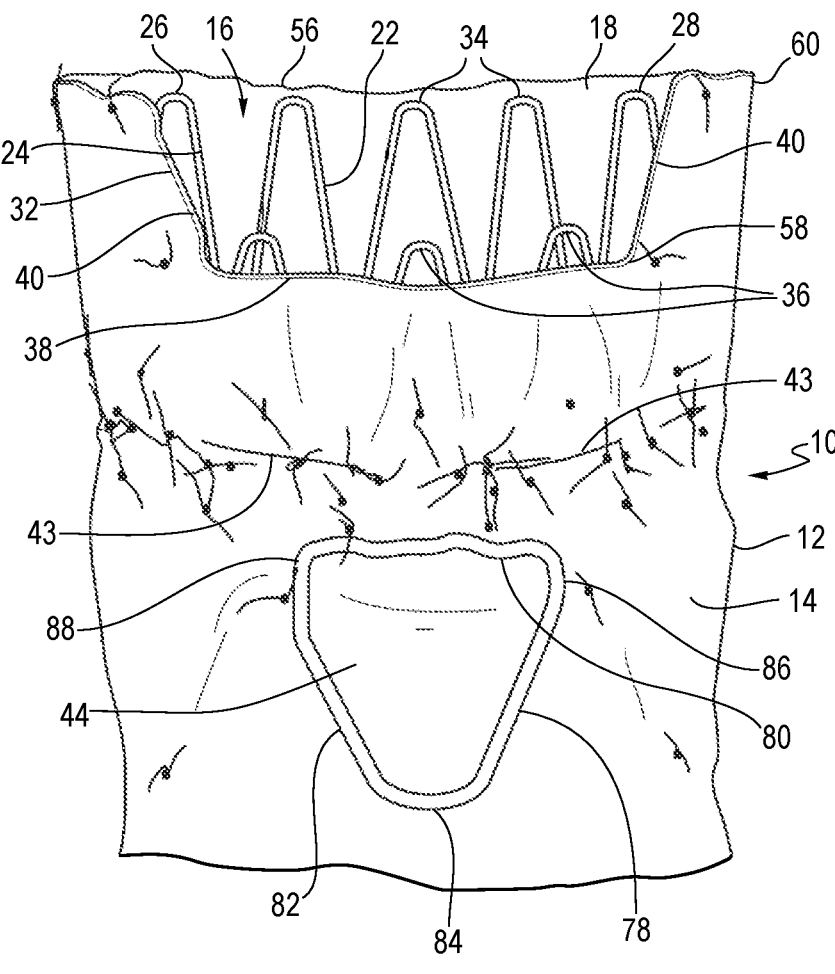
FIG. 1 is a front view of a proximal end portion of a prosthesis such as a stent graft.

In this disclosure, the terms 'proximal' and 'distal' refer to opposite directions with respect to a prosthesis. 'Proximally' means in a direction from a distal toward a proximal end of the prosthesis and 'distally' means in a direction from a proximal toward a distal end of the prosthesis.

The particular embodiments described below are configured such that the proximal end is in use closest to the patient's heart, meaning that in these embodiments the term 'proximal' refers to a location which in use is closest to the patient's heart and the term distal refers to a location which in use is farthest from a patient's heart. However, other embodiments can be configured such that the distal end is in use closest to the patient's heart.

The present invention seeks to provide an improved endoluminally implantable medical device and method. Specifically, the present invention provides a novel and improved stent graft for treatment of a curved aortic lumen, and in particular the aortic arch.

FIGS. 1 to 7 show an endoluminally implantable medical device in the form of a prosthesis 10. The prosthesis 10 is shown as a stent graft and is configured for implantation into a curved lumen, such as the aortic arch and descending thoracic aorta as is described below. The prosthesis 10 also can be configured for implantation into lumens with different topologies, curved or not. Except as otherwise indicated, the prosthesis is described in an expanded condition, which is fully expanded and unrestricted. The prosthesis 10 comprises a graft in the form of a tubular graft body 12 including a sidewall 14 with an internal lumen 16 therethrough. The tubular graft body 12 has a proximal end 18 and a distal end 20 (shown in FIGS. 2 and 3). The tubular graft body 10 in this embodiment is made of a woven polyester fabric, but in other embodiments it can be made of any suitable flexible and biocompatible material, including but not limited to PTFE, ePTFE and the like.

Figure 2:
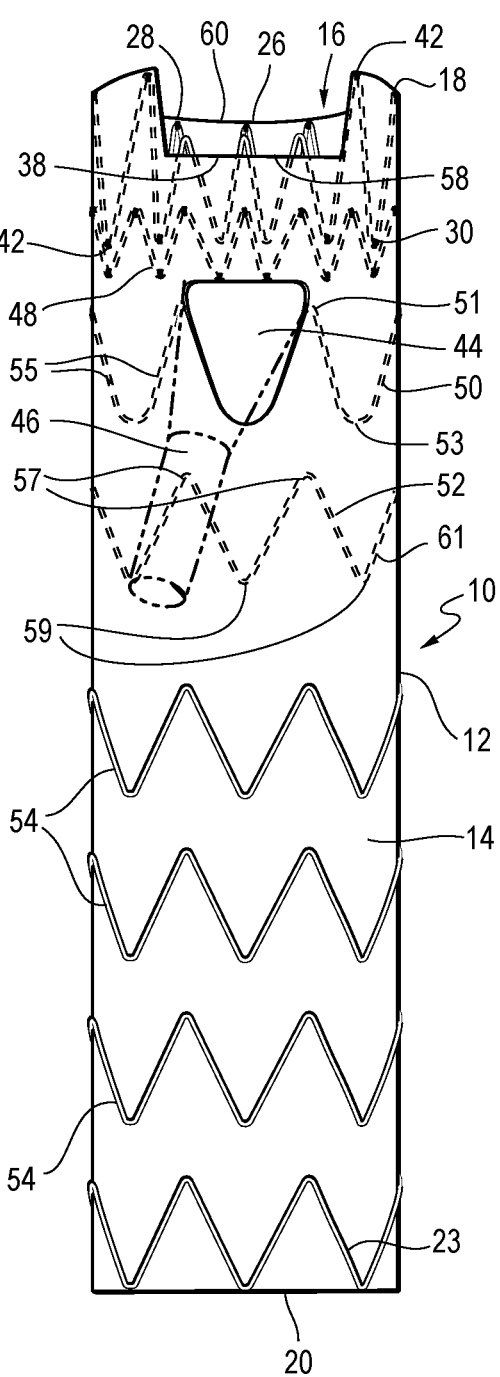
FIG. 2 is a schematic diagram showing a front view of the prosthesis of FIG. 1.
Figure 3:
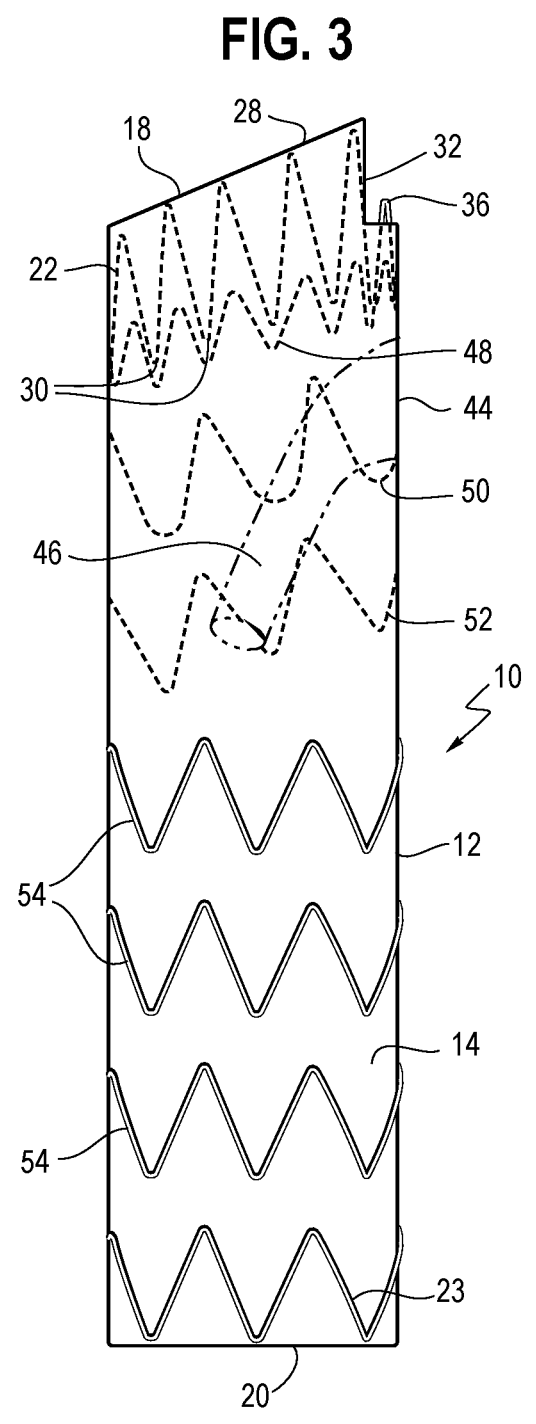

As shown in the partial view of the prosthesis 10 of FIG. 1, and in FIGS. 2-3, a first proximal sealing stent 22, which is at least partially disposed within the lumen 16, is disposed on an interior surface of the tubular graft body 12. The first proximal sealing stent 22 is configured to seal the proximal end 18 of the tubular graft body 12 against an aortic wall. The internal sealing stent 22 presents an essentially smooth outer surface that seals against the aortic wall. The first proximal sealing stent 22 may include struts 24 with bends/apices 26.

The apices 26 of the first proximal sealing stent 22 include proximal apices 28 and distal apices 30 (shown in FIGS. 2 and 3). A further shown in FIGS. 1-3, at the proximal end 18 of the tubular graft body 12, there may be a scalloped fenestration 32 ("scallop"), described in further detail below, which is configured and designed to accommodate an artery opening from the aorta, for example one of the arteries of the aortic arch to provide blood flow thereto. Suitable structures for a scallop are disclosed and described in U.S. Pat. No. 9,539,123 to Hartley et al. ("Fenestrated Stent Grafts"), issued on Jan. 10, 2017, the entire disclosure of which is incorporated by reference herein.

As shown in FIG. 1, the proximal apices 28 of the first proximal sealing stent 22 include body apices 34 and scallop apices 36, as will be discussed in further detail below. The scallop 32 includes a lateral edge 38 and two longitudinally extending sides 40. As shown in FIGS. 2 and 3, the bends/apices 26 of the first proximal sealing stent 22 are attached to the tubular graft body 12 by one or more sutures 42, preferably at each of the apices. Although other suturing methods are contemplated. Suitable methods of suturing apices to a stent graft and suture configurations are disclosed and described in U.S. Pat. No. 7,238,198 to Hartley, et al. ("Stent-Graft Fastening), issued on Jul. 3, 2007, the disclosure of which is incorporated by reference herein in its entirety.

As further shown in FIGS. 1-3, a fenestration 44, as will be discussed in further detail below, is disposed in the sidewall 14. As shown in FIGS. 2 and 3, an internal branch 46 (FIGS. 2 and 3) is disposed within the lumen and extends from the fenestration toward an end in the stent graft. In FIGS. 2 and 3, the branch is shown extending distally. However, a proximally extending branch is also contemplated. The fenestration 44 and internal branch 46 are configured and designed to accommodate artery branching (such as the Left Subclavian Artery (LSA) from the aortic arch. The fenestration 44 may be constructed with a trough. Suitable trough structures and the methods of making them are disclosed and described in U.S. Pat. No. 11,446,168 to Roeder et al. ("Prosthesis With Side Branch and Method of Making"), issued on Sep. 20, 2022 and U.S. Pat. No. 10,537,419 to Kratzberg et al. "Prosthesis With Branched Portion"), issued on Jan. 21, 2020, the entire disclosures of which are incorporated by reference herein in their entireties.

FIGS. 2 and 3 show front and side views of the full-length prosthesis 10 of FIG. 1. As shown, in addition to the first proximal sealing stent 22, there is a series of additional stents disposed distally of the first proximal sealing stent, including nested stent 48, fenestration supporting stent 50, auxiliary stent 52, body stents 54, and distal end sealing stent 23, which are described in detail below. The stents are distributed longitudinally along the graft body 12. Each of the stents comprises a plurality of peaks and valleys connected in a zig-zag arrangement to form a ring around the tubular graft body 12, on the inside or outside of the tubular graft body 12, or within the graft body 12 itself, with adjacent peaks and valleys (apices) being connected by struts. It will be understood that the term 'peaks' generally refers to one set of apices (proximal or distal) and the term 'valleys' refers to the other set of apices. In the embodiments described, the term 'peaks' is used for proximal apices and the term 'valleys' is used for distal apices; however, it will be appreciated that in other embodiments the terms can be used the other way around. In the embodiments shown in the figures, each stent is a self-expanding stent, some of which are made of stainless steel and some of which are made of Nitinol. However, other materials or forms of stent can also be used. For example, in other embodiments, any of the stents can be made of stainless steel or a shape memory alloy, such as Nitinol. In some embodiments, the stents can be balloon-expandable. Other embodiments of the prosthesis 10 can include any combination of stents from the group of stents. It should be appreciated that any of the stents described could be disposed on the outside of, the inside of, or within, the graft material of a stent-graft.

The stents are fastened to the tubular graft body 12 with stitches/sutures in any known manner, for example, as shown in FIG. 1 the stents are attached at the apices. Alternatively or additionally, the stents may be attached to the tubular graft body fully or partially along the length of the struts by way of individual sutures, running sutures, or the like. The stitches may be made of braided polyester and monofilament polypropylene suture. In other embodiments, any other suitable forms of attachment or stitch materials can be used for any of the stents.

Figure 6:
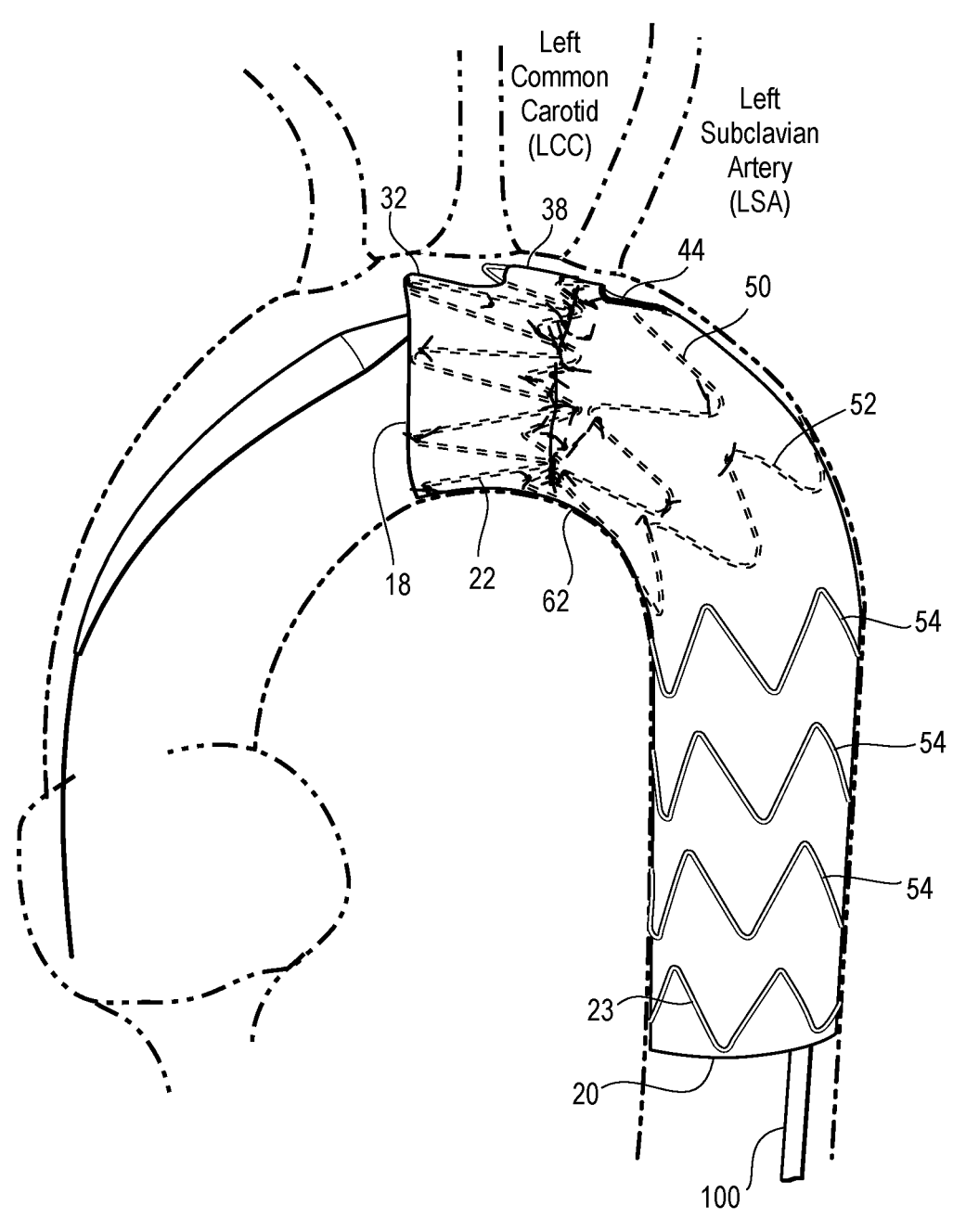
FIG. 6 shows the prosthesis of FIG. 1 in a partially deployed state, as it would be when placed within the aortic arch and descending thoracic aorta of a patient.
Figure 7:
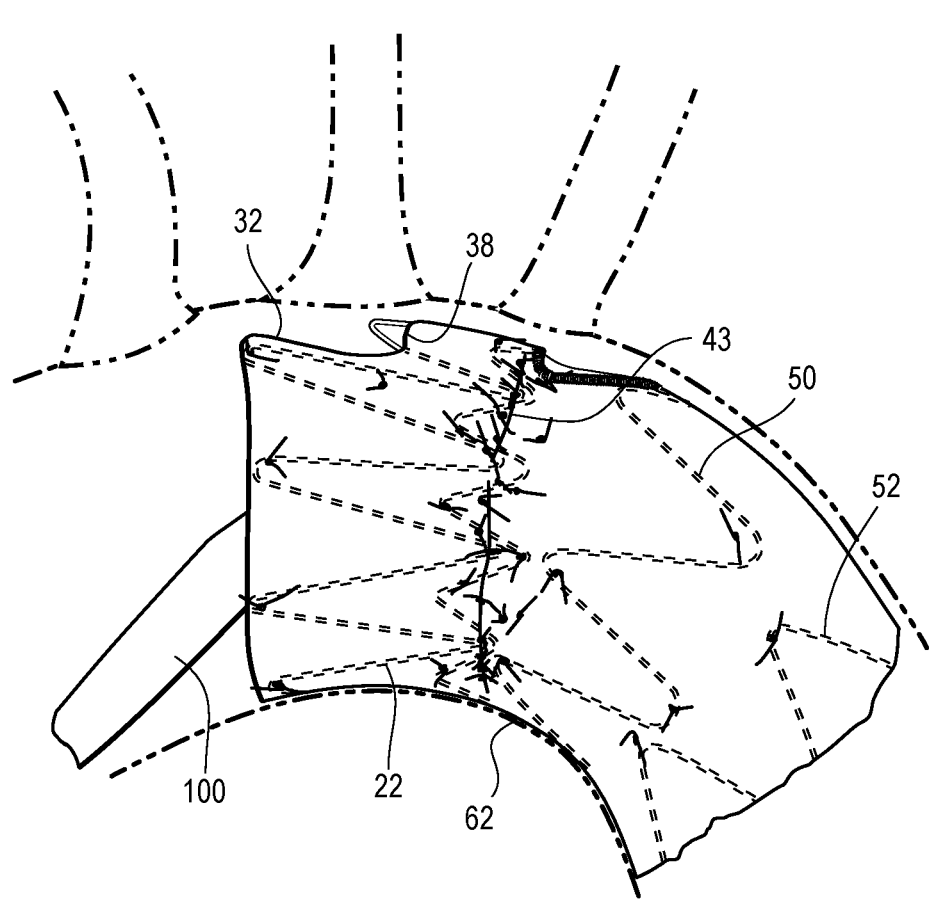
FIG. 7 shows a partial view of the proximal end portion of the prosthesis of FIG. 6 in a fully deployed state, as it would be when deployed within the aortic arch of a patient.

As shown scallop 32 is located at the proximal end 18 of the tubular graft body 12, as shown in FIGS. 1, 2 and 3. The scallop 32 is a cut-out or bight in the material of the tubular graft body 12. The scallop 32 is sized and shaped so that, when the prosthesis 10 is deployed at a target region in a vessel of a human, the scallop 32 accommodates the opening of an adjacent branch vessel. That is, the scallop 32 is sized and shaped and configured so that its edge forms a seal around the opening of a branch vessel without occluding the opening with graft material. In this embodiment, once the prosthesis 10 is in its fully deployed state within the aortic arch of a patient, the graft material at the lateral edge 38 of the scallop 32 will be adjacent to the perimeter of the opening of, for example, the left common carotid artery. In the fully deployed state, a distalmost part of the scallop 32 is positioned between the openings of the left subclavian artery (LSA) and the left common carotid (LCC) artery, as shown in FIGS. 6 and 7. The scallop 32 in this embodiment tapers in width from a maximum width at a proximal end to a minimum width at a distal end.

A shown in FIGS. 1-3, a transverse or lateral edge 38 at the distal end of the scallop 32 is substantially parallel to the edge of the graft material at the distal end 20 of the tubular graft body 12. In other embodiments it can be more curved or angular in shape than shown. In some embodiments, the scallop 32 can be formed of a single curve. In some embodiments, the scallop 32 can be horseshoe-shaped. Suitable shapes for a scallop are disclosed and described in U.S. Pat. No. 9,539,123 to Hartley et al. ("Fenestrated Stent Grafts"), issued on Jan. 10, 2017, the disclosure of which is incorporated by reference herein in its entirety.

The dimensions of the scallop 32 can be tailored according to the target vessel. As shown in FIG. 2, the scallop 32 has a maximum width of 30 mm, at its proximal end, and a minimum width of 25 mm, at its distal end. The scallop 32 in this embodiment has a depth of 14 mm from its distal end to its proximal end, the proximal end of the scallop 32 being at the proximal end 18 of the tubular graft body 12, as shown in FIG. 3. In other embodiments, the width and depth of the scallop 32 can be any suitable size to accommodate the opening of a target vessel. For prostheses intended to be deployed in the aortic arch, it is preferred that scallop 32 is configured to allow for a proximal sealing zone of 10-20 mm, where the proximal sealing zone is the zone between the scallop 32 and a nearest fenestration, such as fenestration 44 described in detail below. Although the first proximal sealing stent 22 at the level of the scallop 32 provides some sealing, the proximal sealing zone provides the majority of the sealing. The size of the sealing zone can be varied to be suitable for the distance between the vessels in the patient. The sealing zone is preferably at least 10 mm, more preferably at least 15 mm. In this embodiment the sealing zone is 16 mm.

Returning again to FIG. 1, at the proximal end 18 of the prosthesis 10 the graft material forms a proximal edge 56, which runs around the circumference of the tubular graft body 12. The scallop 32 defines first and second circumferential regions 58, 60 at the proximal end 18. The first circumferential region 58 coincides and is coterminous with the scallop 32 and the second circumferential region 60 makes up the remainder of the circumference such that the first and second circumferential regions make up a complete circumference of the prosthesis. The first circumferential region 58 is smaller than the second circumferential region 60, meaning the second circumferential region 60 makes up a majority of the circumference of the graft at the proximal end 18.

Figure 4:
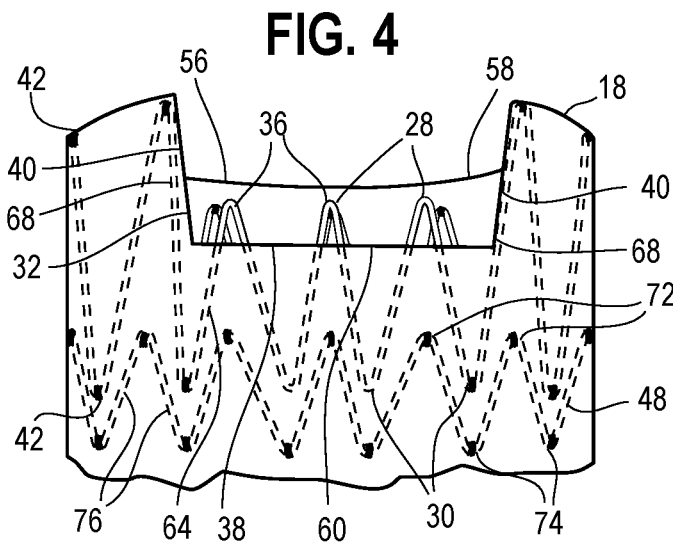
FIG. 4 is an enlarged front view of the proximal end portion of the prosthesis of FIG. 1.

The first proximal sealing stent 22 of the prosthesis 10 is the endmost stent disposed at the proximal end 18 of the tubular graft body 12. As previously discussed, the apices 26 of the first proximal sealing stent 22 include a set of proximal apices 28 and a set of distal apices 30, as shown in FIG. 4. The set of proximal apices 28 includes scallop apices 36, which are located in the first circumferential region 58 (in other words at the scallop 32), and body apices 34, which are located in the first circumferential region 60 (in other words circumferentially outside the scallop 32).

The first proximal sealing stent 22 can therefore be said to comprise a plurality of stent units, each stent unit comprising first and second struts 24 connected by a proximal apex 26. Neighboring stent units are connected by distal apices 30 to form a stent ring. The plurality of stent units includes scallop units and body units, where each scallop unit has a proximal apex located at the scallop (in the first circumferential region 58) and each body unit has a proximal apex located in the second circumferential region 60. Each scallop unit comprises a pair of struts 24 connected by a scallop apex 36. Similarly, each body unit comprises a pair of struts 24 connected by a body apex 34. The body units that are adjacent to the scallop, which support the scallop, and in particular support the sides of the scallop 32, are referred to as supporting units 39. Of the supporting units 39, the struts that are adjacent to the scallop run along the edge of the scallop (See FIG. 2). A supporting unit 39 is disposed on each side of the scallop 32.

As shown in the Figures, the first proximal sealing stent 22 is an internal stent; in other words, it is disposed around an interior surface of the tubular graft body 12. However, it may be an external stent or it can be disposed within the thickness of the graft material. The first proximal sealing stent 22, may have sixteen to twenty-eight apices 26, eight to fourteen of which are proximal apices 28 and eight to fourteen of which are distal apices 30, although in practice this can be varied for example in dependence on the prosthesis diameter. Hence, there can be any suitable number of apices 26. It is preferred that there are the same number of proximal apices 28 and distal apices 30, but it is not necessary. Similarly, of the fourteen proximal apices 26 in the embodiment shown, there are three scallop apices 36 and eleven body apices 34; however, the number of scallop apices can be varied based on the size of the scallop. In other embodiments there can be any number of scallop apices 36 and any number of body apices 34, provided of course that the scallop apices can be located within the first circumferential region, that is at the scallop 32. It is preferred, however, that there are more body apices 34 than there are scallop apices 36.

The body apices 34 are all disposed at the proximal edge 56 of the graft material, as best shown in FIG. 1. It is preferred that all the body apices 34 are disposed at the proximal edge 56 of the graft material in order to most effectively seal the proximal end 18 of the tubular graft body 12. However, in other embodiments, the body apices 34 can be variously disposed further distally or proximally than shown.

The scallop apices 36 are disposed distally of the body apices 34 that are adjacent to the scallop 32. In particular, it has been found to be beneficial that the scallop apices 36 do not extend all the way to the most proximal end of the tubular graft body 12. This arrangement reduces the stent struts and apices in the scallop 32 that might otherwise impinge upon the vessel wall at the location of the branch vessel and thereby reduces the possibility of trauma or damage to the vessel. In this manner, the first proximal sealing stent 22 can itself be said to include a scallop at its proximal end in the region of the scallop 32 in the tubular graft body 12.

The set of distal apices 30 are all disposed distally of the distal end 20 of, in particular of a distalmost edge of, the scallop 32, as can be seen in FIGS. 2, 3, and 4. It is preferred that all of the distal apices 30, or at least a majority thereof, are disposed at least longitudinally level with, or distally of, a distal end of or a distalmost point on the scallop 32, which improves the ability of the first proximal sealing stent 22 to seal the full perimeter of the scallop 32. As shown in FIG. 2, the distal apices 30 are also all aligned with one another. As shown in FIG. 3, the longitudinal positions of the distal apices 30 may vary around the circumference of the tubular graft body 12. In particular, the distal apices 30 are most distal at an inner curve region 62 (shown in FIG. 6) of the prosthesis 10, where the inner curve region 62 is the region configured to be deployed in the inside of the curve of the body lumen. The distal apices 30 linearly become more proximal in both circumferential directions away from the inner curve region 62 such that they are most proximal diametrically opposite the inner curve region 62. In this way, the distal apices describe an ellipse which lies in a plane which is non-perpendicular to the longitudinal axis of the prosthesis. In other embodiments, the distal apices 30 can all be longitudinally level. Furthermore, in other embodiments, the distal apices can be unaligned.

The scallop apices 36 are located at the distal end of the scallop 32. Referring again to FIGS. 1 and 4, the body apices 34 are all covered, that is to say overlapped, by graft material. The scallop apices 32, however, extend proximally of the proximal edge 16 of the tubular graft body 12 at the scallop 32, in other words extend proximally of the distal end of the scallop, uncovered by the graft material. As a result, a majority, but not all, of the first proximal sealing stent 22 is covered by graft material. Nevertheless, the graft covers at least a majority of each of the interstices between the peaks of the first proximal sealing stent 22. In other words, the spaces between struts 24 adjoining Neighboring proximal apices 36 of the first proximal sealing stent 22 are each substantially or completely overlapped by graft material.

However, as shown in FIGS. 13-16, the proximal apices 28 of the first proximal sealing stent 22 do not extend beyond the graft material (that is to say that the proximal stent may be entirely covered by graft material). This can be the case for example where the proximal stent is made of Nitinol. However, it has been found to be beneficial in some embodiments such as the embodiment of FIG. 1 to incorporate scallop apices 336 that extend beyond the graft material, the reasons for which are explained below.

As described, the apices 28 of the first proximal sealing stent 22 are connected by struts 24. Each of the scallop apices 36 is connected to Neighboring distal apices 30 by first and second scallop apex struts 64. Similarly, the body apices 34 are each connected to Neighboring distal apices 30 by first and second body apex struts 66.

As best shown in FIG. 4, the may struts 24 vary in length around the circumference of the first proximal sealing stent 22, creating a taller segment and a shorter segment of the stent. In particular, struts 64 at the scallop 32 are shorter than the struts 66 adjacent to the scallop 32 at each side. In other words, the first and second struts 64 of each scallop unit are shorter than the first and second struts of each supporting unit 39. The shorter scallop apex struts 64 reduce the volume of stent material at the scallop 32 to keep the scallop substantially clear. At the same time, the longer struts 66 of the supporting units 39 help to support and seal the prosthesis adjacent to the scallop.

The scallop apex struts 64 are preferably short to avoid, as far as possible, obstructing the scallop 32. However, in practice, it has been found that it is beneficial for a minimum strut length to be used to achieve improved flexibility and elasticity of the stent and avoid undesired plastic deformation in use, particularly in the region of a branch vessel. The minimum strut length depends on the dimensions of the target vessel and the material of the struts. The minimum strut length in some embodiments, such as the embodiment of FIG. 1, results in the scallop apices 36 extending beyond the graft material, as shown in FIG. 1. Despite this, at least a majority of each of the scallop units is overlapped by graft material. Furthermore, as indicated above, it should be appreciated that it is not necessary in all embodiments for the scallop apices to extend beyond the graft material. In some embodiments, for example where the proximal stent is made of Nitinol, the minimum strut length is such that the scallop apices 36 can be positioned distally of the proximal edge 16 and distal end of the scallop and thereby be covered by graft material. In the embodiment shown, the strut length of the scallop units is 17 mm.

The scallop apex struts 64 of the embodiment shown in FIGS. 1 to 7 are shorter than a majority of the body apex struts 66. In other embodiments, the scallop apex struts 64 are all shorter than any of the body apex struts 66. However, it is particularly beneficial that the scallop apex struts 64 are shorter than the body apex struts 66 that are adjacent to the scallop 32 (in other words those in the supporting units 39 as described above). In some embodiments, the scallop apex struts 64 are shorter than just those pairs of body apex struts 66 adjacent to the scallop. In other words, it is particularly beneficial that the first and second struts of the scallop units are shorter than the first and second struts of the supporting units 39. In the embodiment shown, the scallop apex struts 64 are all the same length, but in other embodiments they can be of different lengths.

The apices 28 may not be uniform around the circumference of the first proximal sealing stent 22. Stents typically have apices of consistent radii of curvature around their circumference, which produce uniform radial forces around the stent. The first proximal sealing stent 22, however, has apices 28 of different radii of curvature around its circumference. In particular, the first proximal sealing stent 22 may include at least one scallop unit with a proximal apex which is more rounded or has a greater radius of curvature than the proximal apex of at least one preferably substantially diametrically opposite body unit. For example, the scallop apices 36 all have a greater radius of curvature than each of the body apices 34. The increased roundedness of the scallop apices 36 better distributes the radial force exerted by the stent at those apices, making them blunter and reducing the vessel pressure/area, thereby reducing the potential traumatic or erosive effect of the scallop apices 36 on the tissue of the vessel wall. It may also assist with sealing.

The scallop apices 36 may also be more rounded than all the other apices 26 of the first proximal sealing stent 22. The less rounded body apices 34 and distal apices 30 relatively reduce the volume and increase the elasticity of the first proximal sealing stent 22. This effect is particularly beneficial in the region of the stent 22 circumferentially opposite the scallop 32, which in use is positioned at the interior of the curvature in the vessel. In this embodiment, the distal set of apices all have the same radius of curvature. Furthermore, in this embodiment, all the apices of the stent that are located in the second circumferential region have the same radius of curvature.

As shown in FIGS. 1 to 7, each of the scallop apices 36 has a radius of curvature of 1 mm, each of the body apices 34 has a radius of curvature of 0.5 mm, and each of the distal apices 30 has a radius of curvature of 0.5 mm. It has been found to be particularly advantageous for the scallop apices 36 to have a radius of curvature approximately double that of the body apices 34. In embodiments, the scallop apices may have 1.5 to 2.5 times the radius of curvature of the body apices 34. It has been found to be even more advantageous still for the scallop apices 36 to have a radius of curvature approximately double that of all the remaining apices 28 (namely the body apices 34 and the distal apices 30). In other examples, the scallop apices may have 1.5 to 2.5 times the radius of curvature of the remaining apices. It is to be noted that the scallop apices 36 need not all have the same radius of curvature in every embodiment. Similarly, the body apices 34 do not all need to have the same radius of curvature as one another. Similarly, the distal apices 30 do not all need to have the same radius of curvature in every embodiment.

The first proximal sealing stent 22 may have a proximal-distal length from a proximal end of the stent 20 to a distal end of the stent 20 which varies around the circumference of the prosthesis 10, as shown in FIG. 3. In particular, the length of the proximal stent increases in both circumferential directions from the inner curve region 18 of the prosthesis 10, providing the first proximal sealing stent 22 with a wedge shape.

Figures 11, 12:
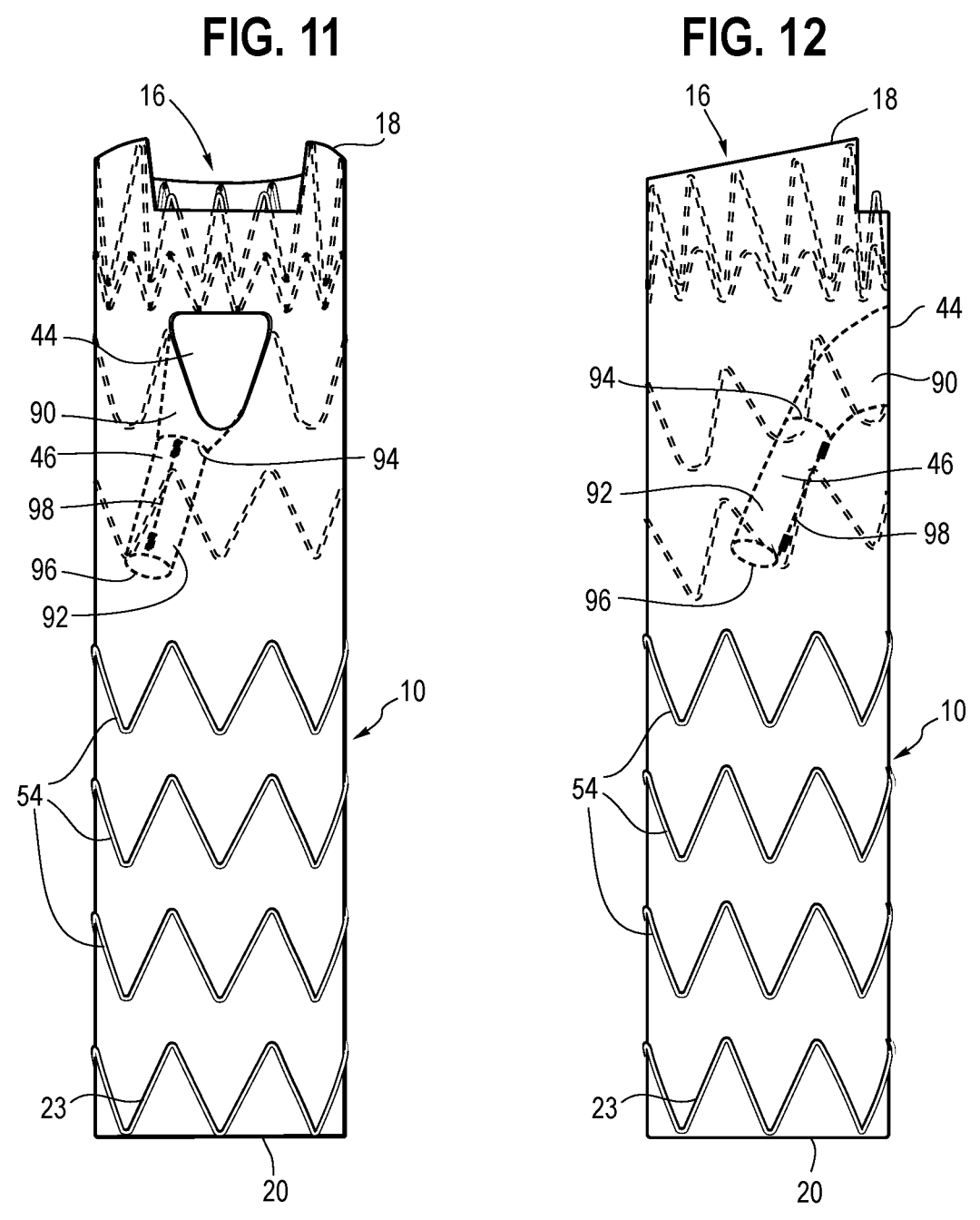

Furthermore, as shown in FIGS. 3 and 12, the proximal end of the first proximal sealing stent 22 has a taper such that the longitudinal location of the first end of the stent increases in a proximal-distal direction in both circumferential directions from the inner curve region. In particular, the longitudinal location of the first end of the stent becomes more proximal in both circumferential directions from the inner curve region. The taper tapers away from the scallop 32. In addition, in this embodiment the proximal end of the graft body (effectively the plane of the end of the graft body) is slanted with respect to the sidewall 14 (and the longitudinal axis of the graft body) so that it forms an obtuse angle with respect to the sidewall 14 at the inner curve region 18 at the proximal end of the graft body. In this embodiment, the proximal end of the tubular graft body 12 aligns with the proximal end of the first proximal sealing stent 22 around at least a majority of the circumference of the proximal end of the tubular graft body 12, in this embodiment around the entirety of the proximal end of the tubular graft body 12 except for the scallop 32. In particular, the proximal end of the tubular graft body 12 is substantially equidistant from the proximal end of the first proximal sealing stent 22 around at least a majority of the circumference of the proximal end of the tubular graft body 12, in this embodiment around the entirety of the proximal end of the tubular graft body 12 except for the scallop 32. The majority of the proximal end 18 of the tubular graft body 12 lies on a flat plane which is generally parallel to a plane on which the body apices 34 are arranged. In particular and as described above, in this embodiment, all of the body apices 34 are at the proximal edge 56 of the graft material, and in particular are about 1 mm from the edge 56. The body apices can be slightly further spaced from the proximal edge of the graft material, but are preferably all within 2 mm of the proximal edge of the graft material.

In more detail, among the struts 24, the body apex struts 66 vary in length around the circumference of the first proximal sealing stent 22, as shown in FIG. 3. In this embodiment, pairs of body apex struts 66 nearer the scallop 32 may be longer than those farther from the scallop 32, a pair of body apex struts 66 being two body apex struts 6 that meet at a common proximal apex 28, otherwise referred to as a stent unit. The length of each successive pair of body apex struts 66 is varied linearly so that the body apices 34 are arranged in a straight line. The body apices 34 nearest the scallop 32 extend farther proximally than those circumferentially opposite the scallop 32, creating the taper, shown in FIG. 3 as an offset A. FIG. 3 shows the tapered profile and wedge shape when the prosthesis 10 is viewed in profile. The proximal end 18 of the tubular graft body 12 is also tapered in the first circumferential region 58 according to the same profile and taper. The lengths of the body apex struts 54 vary by equal increments to both sides of the scallop 32 so that the first proximal sealing stent 22 is bilaterally symmetric.

As can be seen in FIG. 3, in this embodiment the taper at the proximal end 18 of the first proximal sealing stent 22 comprises, in each circumferential direction from the inner curve region 62, the body apices 34 being offset from each other in the proximal-distal direction and being disposed in increasingly proximal locations. In this embodiment, all of the body apices 34 contribute to the taper; however, in other embodiments, one or more body apices 34 may be out of line while still retaining an overall taper. It is preferred that the taper comprises, in each circumferential direction from the inner curve region, at least three preferably adjacent apices at the first end of the first stent offset from each other in the manner described. The offsets between adjacent body apices 34 are substantially the same to form a linear taper. In this embodiment, the taper, that is the offset A, is 15 mm, which has been found to provide optimum performance. Preferably, the taper is from about 5 mm to about 20 mm, more preferably from about 10 mm to about 20 mm, most preferably from about 13 mm to about 17 mm.

With a stent-graft that has stents with struts of uniform length around its circumference, adjacent stents may interfere with one another in a curved section of a vessel. When such a stent-graft is deployed in a tortuous vessel, there is therefore a greater possibility that it will sit proud of the vessel wall—extending tangentially from the curvature of the vessel—leading to incomplete sealing and poor alignment within the vessel.

By contrast, the wedge shape of the first proximal sealing stent 22 accommodates the curvature of the prosthesis 10 when positioned in a curved vessel, such as the aortic arch. In its deployed state, the prosthesis 10 is oriented within the vessel so that the narrow end of the wedge shape is located at the interior of the curve of the vessel. The wedge shape and taper are configured so that, when the prosthesis 10 is deployed, the line formed by the body apices 34—and also the proximal end of the graft body, in particular the proximal edge 16 of the tubular graft body 12 in the first circumferential region 58—deploys substantially perpendicularly to the curve of the vessel, as shown in FIG. 7. In this way, the first proximal sealing stent 22 of the prosthesis 10 exerts against the vessel wall at an optimum angle, enabling the graft material of the prosthesis 10 to seal flush against the vessel wall.

As shown, the first proximal sealing stent 22 has body apex struts 54 that vary in length from 19 mm, at the pair of struts (or stent unit) circumferentially opposite the scallop 32, to 27 mm, at the pairs of struts (or stent unit) nearest the scallop 32; the length of each pair of body apex struts 54 increasing by an increment of 2 mm per successive body apex 34. The lengths of the body apex struts 54 that form the wedge shape can be tailored according to the length of the expected attachment area and the optimum angle of taper for the vessel geometry.

Figure 8:
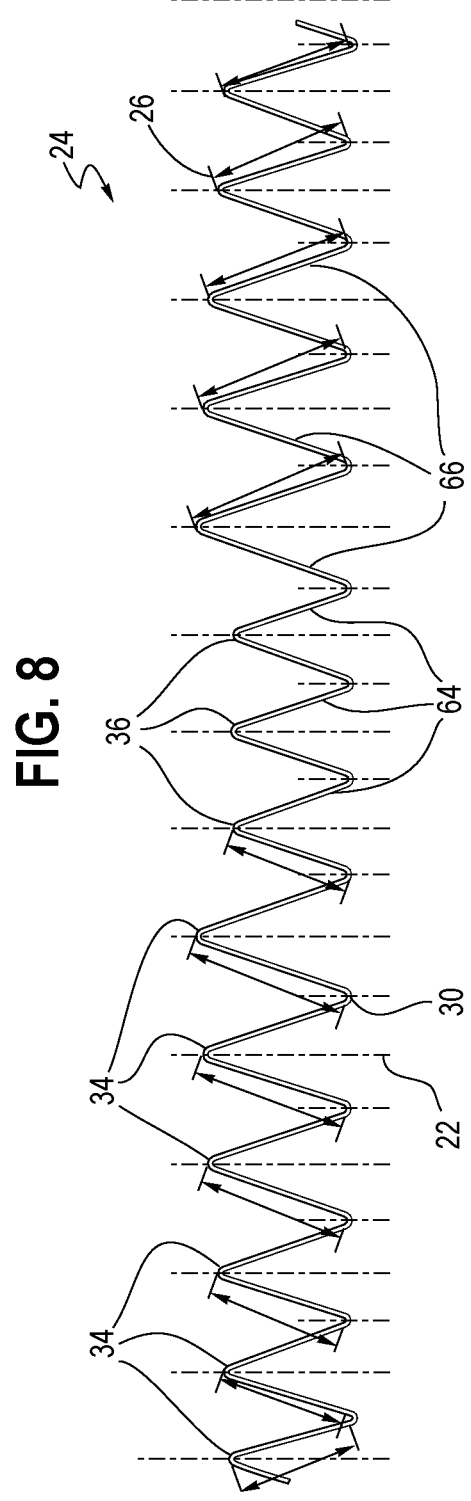
FIG. 8 is a schematic diagram of a stent suitable for use with a prosthesis of the invention.
Figure 9:
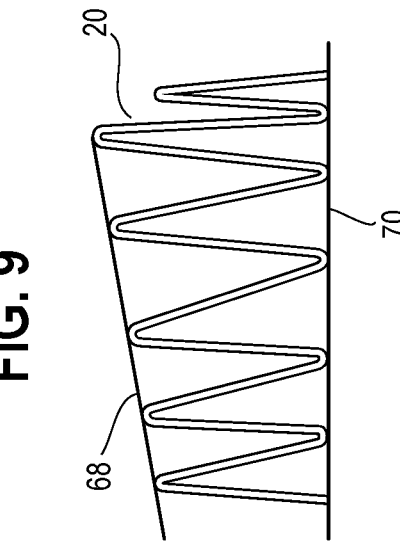
FIG. 9 is a second partial schematic diagram of the stent of FIG. 8.
Figure 10:
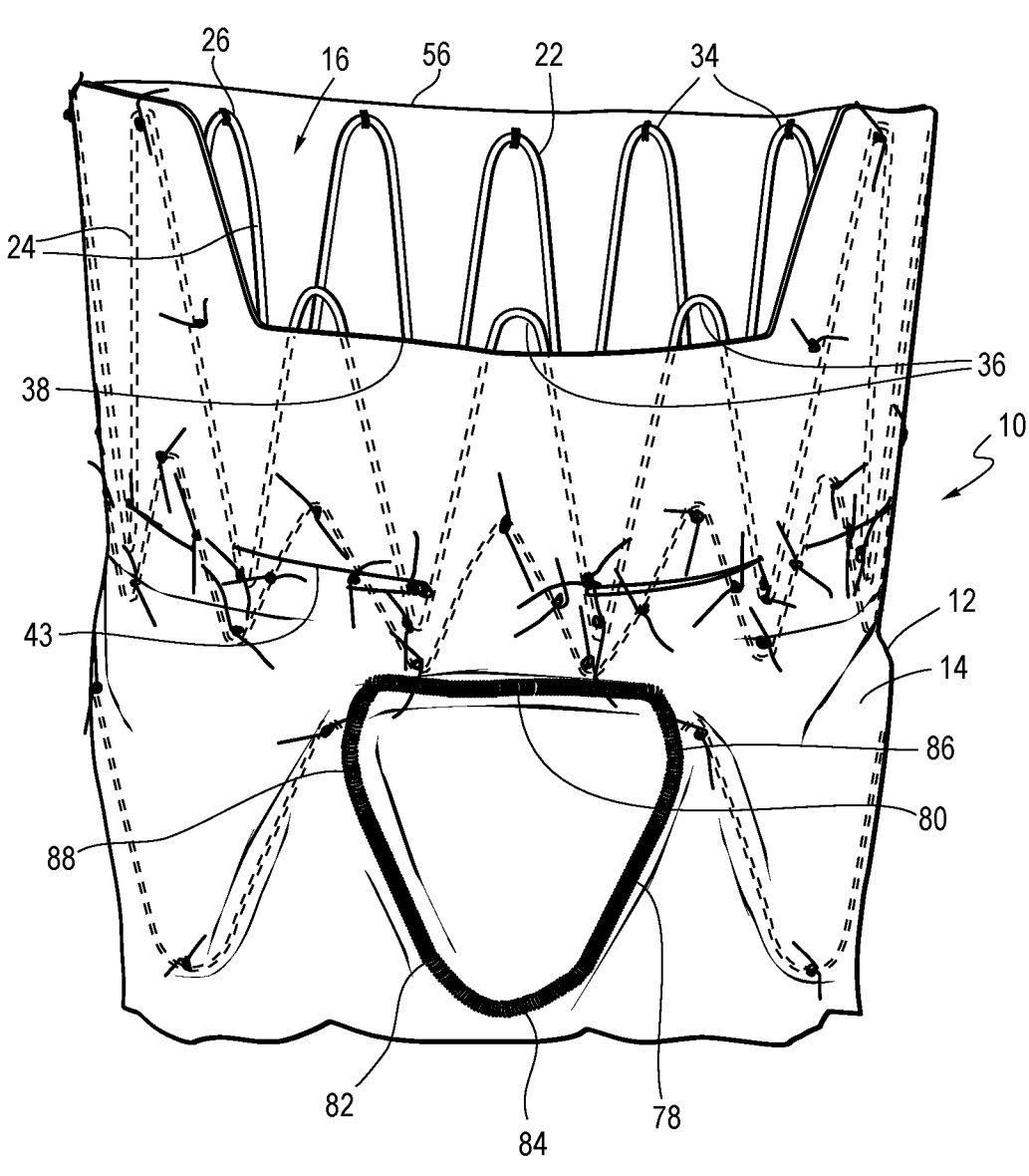
FIG. 10 is a view of a proximal portion of a prosthesis including the stent of FIGS. 8 and 9.

FIGS. 8, 9, and 10 show a further embodiment of the first proximal sealing stent 22. Here, the first proximal sealing stent 22 is the same as the first proximal sealing stent 22 in FIGS. 1 to 7 in all aspects except the lengths of its struts 26. FIG. 8 shows the variation in length of the struts 26 around the circumference of the first proximal sealing stent 22. In this embodiment, the body apex struts 64 of the first proximal sealing stent 22 taper in length from 22 mm, at the pairs of struts (or stent units) nearest a scallop apex 36, to 17 mm, at the pair of struts (or stent unit) farthest from a scallop apex 36; the length of successive pairs of body apex struts 64 varying by an increment of 1 mm per body apex 34. The body apices 34 are arranged along a line 68 and the distal apices 30 are arranged along a line 70. This creates a wedge shape profile in the stent 22 as shown in FIG. 9. By comparison to the first proximal sealing stent 22 of FIGS. 1 to 7, the proximal end of the stent in this embodiment can provide a shallower taper or offset A in the wedge shape of the stent 20. FIG. 10 shows the further embodiment of the first proximal sealing stent 22 disposed at the proximal end of the prosthesis 10. In all other aspects, the prosthesis 10 of FIG. 10 is the same as that of FIGS. 1 to 7. Other embodiments of the stent 22 can have body apex struts 34 of any length suitable for the target vessel.

The variation in length between the body struts 66 can be non-linear. Furthermore, it is not excluded that a proportion of the body apices 34 can be variously disposed farther proximally or distally, and/or a proportion of the body apex struts 66 can be variously shorter or longer than the described arrangement while still providing a generally wedge-shaped stent and taper. It has been found to be particularly advantageous for the proximally endmost stent of the prosthesis 10 to utilize a wedge shape. However, any of the other stents of the prosthesis 10 can also, or alternatively, have a wedge shape.

It should be appreciated that some advantages provided by features of the first proximal sealing stent 22 can be achieved independently of any or all of the other components of the prosthesis 10, for example without the scallop 32 and fenestration 44.

Similarly, it should be appreciated that some advantages achieved by the variation in roundedness of the apices 26 of the first proximal sealing stent 22 can be realised without a variation in the lengths of the struts 24 of the first proximal sealing stent 22. Equally, some advantages achieved by the variation in length of the struts 24 can be realised without a variation in the roundedness of the apices 26. Similarly, some advantages achieved by the difference in length between the scallop apex struts 64 and body apex struts 66 can be realized without a variation in length between the body apex struts 66. Similarly, some advantages achieved by the wedge shape of the first proximal sealing stent 22 can be achieved without scallop apex struts 64 or scallop apices 36.

With reference to FIGS. 2, 3, and 4, the prosthesis also includes a nested (or sealing) stent 48, disposed distally of and adjacent to the first proximal sealing stent 22. As shown in FIG. 4, the nested stent 48 has a set of proximal apices 72 and a set of distal apices 74 connected by struts 76. The struts 76 and apices 72, 74 form a series of peaks and valleys. In contrast to the first proximal sealing stent 22, the nested stent 48 is radially symmetric. In particular, in the embodiment shown, the nested stent 48 has struts 74 of uniform length and apices 72, 74 with uniform radius of curvature around its circumference. In this embodiment, in contrast to the other stents of the prosthesis 1, the nested stent 48 is made of Nitinol. However, as described above, in other embodiments the nested stent 48 can be made of stainless steel or any other suitable stent material. Further, because the nested stent 48 in this particular embodiment is made of Nitinol it is correspondingly also made of a thinner gauge of wire than the stainless steel first proximal sealing stent 22 is, though this is not necessary in every embodiment.

The proximal apices 72 of the nested stent 48 are positioned so that each peak of the nested stent 48 is nested between a respective pair of valleys of the first proximal sealing stent 22 (in other words between neighboring pairs of distal apices 30). In this way, the nested stent 48 provides increased flexibility and increased control of the radial force, and can improve sealing at the proximal portion of the prosthesis 10 for example by reducing graft infolding. This can allow for a first proximal sealing stent 22 with fewer apices to be used which can be better for the patient. The nested stent 48 can also enable better control of the deployment of the prosthesis 10 and help the prosthesis 10 to keep its structure after having been crimped in a sheath for delivery.

In other embodiments, only some of the proximal apices 72 of the nested stent 48 are nested between distal apices 30 of the first proximal sealing stent 22, although preferably at least a majority of the proximal apices are nested between distal apices of the first proximal sealing stent 22 and it is preferred that the nesting is radially symmetric, as it is in the embodiment of FIG. 1. Similarly, in some embodiments, two or more proximal apices 72 of the nested stent 48 can be nested between the same pair of distal apices 30 of the first proximal sealing stent 22. However, it has been found to be particularly advantageous for each of the proximal apices 72 to be nested between a respective pair of distal apices 30 of the first proximal sealing stent 22.

The struts 76 of the nested stent 48 are shorter than the struts 24 of the first proximal sealing stent 22. In this embodiment every strut of the nested stent 48 is shorter than every strut of the first proximal sealing stent 22. In other embodiments, not every strut of the nested stent 48 needs to be shorter than every strut of the first proximal sealing stent 22 but preferably at least a majority of the struts of the nested stent are shorter than a first strut, preferably a body apex strut, of the first proximal sealing stent 22.

As described above, in the embodiment shown the nested stent 48 is made of Nitinol and the first proximal sealing stent 22 is made of stainless steel. As a result, the nested stent 48 in this particular embodiment produces a generally lower radial force than the first proximal sealing stent 22. However, in other embodiments, either or both of the nested stent 48 and first proximal sealing stent 22 can be made of stainless steel or Nitinol, or any other suitable stent materials.

It should be appreciated that any other stents of the prosthesis 10 could also or alternatively have a stent nested with them in this way. In particular, some advantages provided by the nested configuration can be achieved without features of the first proximal sealing stent 22 such as the variation in roundedness of the apices 26 or the variation in the length of the struts 24. A regular zig-zag stent, for example, disposed at any location in a graft, could similarly be configured in a nested arrangement with a nested stent as described above. This nesting is particularly advantageous for stents that have a sealing function (that is, those stents that act to seal the graft material against the vessel wall).

As shown in the figures, the tubular graft body 12 also includes a fenestration 44. As shown in FIGS. 1 and 10, the fenestration 44 is circumferentially aligned with and distal of the scallop 32. The fenestration 44 is sized and positioned so that, when the prosthesis 10 is in its fully deployed state, the fenestration 44 will accommodate the opening of a branch vessel. In the embodiment shown, the prosthesis 10 is designed to be deployed in the aortic arch, at which point the fenestration 44 aligns with the opening of the left subclavian artery.

In the aortic arch particularly, the landing zone available for a stent-graft is challengingly small. In particular, the distance between the left subclavian and left common carotid arteries, and therefore the distance available between the scallop 32 and fenestration 44, is very short. In the embodiment shown in FIGS. 1 to 7, the length between the scallop 32 and the fenestration 44 is 16 mm. In other embodiments, the length between the scallop 32 and fenestration 44 could be any value suitable to accommodate the distance between openings of Neighboring branches in the target vessel. As described above, for embodiments intended to be deployed in the aortic arch, it is preferred that the scallop 32 is configured to allow for a proximal sealing zone of 10-20 mm.

The fenestration 44 is triangular or trianguloid (in other words substantially triangular) in shape. In this embodiment, the fenestration 44 resembles a triangle with rounded corners: it is formed by three substantially straight edges or sides 78, 80, 82 which are joined by three rounded corners 84, 86, 88. The fenestration 44 is oriented so that it has a top proximal side 66 which is aligned transverse to the longitudinal axis of the tubular graft body 12 (which extends between the proximal end 18 and the distal end 20). The proximal side 80 includes at least a portion that is substantially perpendicular to the longitudinal axis of the tubular graft body 12. The proximal side 80 connects the proximal ends of the two remaining sides 78, 82, which converge to a distal apex at the distal end 63 of the fenestration 44. The flat top of the fenestration 44, formed by the proximal side 80, allows a greater proportion of the fenestration area to be positioned closer to the scallop 32 than would be the case for, for example, a circular or elliptical fenestration. The U-shape formed by the converging sides 78, 82 also acts as a funnel or guide that aids in the positioning of an introducer assembly into the fenestration 44 for cannulation of a side branch therethrough. Suitable fenestration structures and the methods of making them are disclosed and described in U.S. Pat. No. 11,446,168 to Roeder et al. ("Prosthesis With Side Branch and Method of Making"), issued on Sep. 20, 2022 and U.S. Pat. No. 10,537,419 to Kratzberg et al. "Prosthesis With Branched Portion"), issued on Jan. 21, 2020, the disclosures of which are incorporated by reference herein in their entireties. Proximal side 80 may present an unobstructed pathway, which is at least partially unobstructed by stenting and/or stitching.

In some embodiments, the tubular graft body 12 can include a fenestration 44 and not a scallop 32. In other embodiments, the tubular graft body 12 can include a scallop 32 and not a fenestration 44.

The nested stent 48 is provided adjacent to the proximal edge 80 of the fenestration 44. In practice, it is disposed proximally of the fenestration 44, positioned so that the distal apices 74 of the nested stent 48 are disposed adjacent to the proximal edge 80 of the fenestration 44. As with the scallop apices 36, it is preferred that the distal apices 74 are located adjacent to the edge of the graft material without extending across or into the fenestration 44, in order to maximise use of the limited sealing zone available, and maximise sealing in this sealing zone, without occluding the branch vessel opening with stent material. Therefore, in the preferred embodiment shown, the distal apices 74 do not extend beyond the graft material at the proximal edge 80 of the fenestration 44. Equally, the proximal edge 80 of the fenestration 44 does not extend proximally of the distal apices 74 of the nested stent 48.

The prosthesis 10 includes an internal branch graft 46, as shown faintly in FIGS. 2 and 3, and highlighted in FIGS. 11 and 12 (which show the second embodiment of the prosthesis 10 of FIG. 10, the graft 10 of which, by comparison to the first embodiment of FIGS. 1 to 7, has a shallower taper at the proximal end 18 but is otherwise identical). The branch graft 46 extends from the fenestration 44 distally inside the tubular graft body 12. In other words, the internal branch graft 46 extends from the fenestration within the lumen 16 of the stent graft in a distal direction. The branch graft 46 is generally tubular, comprising an internal lumen in communication with the fenestration 44 and the internal lumen 16 of the tubular graft body 12. In this embodiment, the branch graft 46 is made of a woven polyester fabric, but other embodiments can be made of any suitable flexible and biocompatible material. The internal branch graft 46 is provided to assist in guiding a catheter between the internal lumen 16 of the tubular graft body 12 and a branch vessel adjacent to the fenestration 44. In use, a cannula and/or extension graft may be introduced through either the proximal or distal end of the internal branch graft 46 in order to deploy an extension graft in the branch vessel adjacent to the fenestration. For example, a cannula carrying an extension graft may be introduced via the subclavian artery, and from there through the fenestration and the proximal end of the internal branch graft and into the internal branch graft 46. The extension graft can then be deployed so that it spans from the internal branch graft 46 to the branch vessel. In another embodiment, the cannula carrying the extension graft can be introduced through the distal end of the internal branch graft and from there out of the proximal end of the internal branch graft into the branch vessel. The extension graft can then be deployed so that it spans from the internal branch graft 46 to the branch vessel.

The internal branch graft may be straight, curved or helical. Suitable internal branches are disclosed and described in U.S. Pat. No. 11,446,168 to Roeder et al. ("Prosthesis With Side Branch and Method of Making"), issued on Sep. 20, 2022 and U.S. Pat. No. 10,537,419 to Kratzberg et al. "Prosthesis With Branched Portion"), issued on Jan. 21, 2020, the disclosures of which are incorporated by reference herein in their entireties.

The internal branch graft 46 in this embodiment has two distinct portions: a proximal portion 90 and a distal portion 92. The proximal portion 90 has a proximal longitudinal axis and the distal portion 92 has a distal longitudinal axis. The proximal longitudinal axis of the proximal portion 90 intersects with the longitudinal axis of the stent graft at an acute angle and the distal longitudinal axis of the distal portion 92 intersects with the longitudinal axis of the stent graft at an acute angle. The acute angle between the distal longitudinal axis and the longitudinal axis of the stent graft is smaller than the acute angle between the proximal longitudinal axis and the longitudinal axis of the stent graft. This creates a dog-leg or elbow in the internal branch graft 46, as can be seen best in FIG. 12.

The provision of proximal and distal portions 90, 92 for the internal branch graft 46, which have larger and smaller acute angles, respectively, provides a smoother transition between the angle of the left subclavian artery and that of the longitudinal axis of the stent graft. Having the internal branch graft 46 extend distally within the lumen 16 of the stent graft provides for easier cannulation of the left subclavian artery therethrough. However, having the transitionary proximal portion of the internal branch graft 46 avoids an abrupt 90 degree angle between the axis of the left subclavian artery and that of the stent graft. This helps to avoid kinking of devices such as stents being introduced into the left subclavian artery.

In this embodiment, the internal branch graft 46 as a whole is also angled diagonally such that as it extends distally within the internal lumen 16 it also extends laterally from the fenestration 44, as can be seen in FIG. 11. This angulation or twist of the internal branch graft 46 further contributes to providing an easier path and reducing the possibility of kinking, for example, of the small stents being introduced into the artery. The angle of the twist is preferably from 5 to 45 degrees relative to the central longitudinal axis of the tubular graft body 12, measured from the distal longitudinal axis of the distal portion 92 of the branch graft. In this embodiment, the angle of twist is 16 degrees.

The proximal portion 90 and the distal portion 92 of the internal branch graft 46 also differ in their proportions; the distal portion 92 is cylindrical and comparatively elongate and slender, whereas the proximal portion 90 is generally frustoconical, tapering from a larger diameter at its proximal end (where it meets the fenestration 44) to a smaller diameter (matching that of the distal portion 92) at its distal end. The shape of the proximal portion 90 aids the clinician in accessing the internal branch graft 46 with a cannula and/or extension graft, and the shape of the distal portion 92 helps to guide the cannula and/or extension graft more precisely into the target artery. In this embodiment, the proximal and distal portions 90, 92 are of the same length (as measured along their respective longitudinal axes from a proximal end to a distal end) but their lengths are not particularly limited and the proximal and distal portions 90, 92 do not need to be of the same length.

In this embodiment, the distal portion 92 of the internal branch graft 46 includes a supporting structure which helps to maintain its shape and patency. The supporting structure is implemented in a known way, and includes may include a proximal D-ring 94, a distal O-ring 96, and a pair of opposing struts 98 which connect the O-ring and the D-ring along the longitudinal axis of the distal portion 92. The supporting structure in this embodiment is made of Nitinol. Other embodiments can have any suitable supporting structure. Suitable supporting structures for branches are disclosed and described in U.S. Pat. No. 7,914,572 to Hartley et al., ("Side branch stent graft construction"), issued Mar. 29, 2011, the disclosure of which is incorporated by reference herein in its entirety. Additional suitable supporting structures, including radiopaque markers are disclosed and described in US Publication No. 2019/0192275 to Kim, et al. ("Radiopaque Markers on Medical Device"), the disclosure of which is incorporated by reference herein in their entirety. Branches without a supporting structure are also contemplated.

As shown in the Figures, the fenestration 44 may be a single fenestration 44 in the tubular graft body 12 and a single branch graft 46. In other embodiments, there could be any number of fenestrations and branch grafts. In some embodiments, there could be no fenestration or branch graft. In some embodiments, the prosthesis could comprise a fenestration but not a branch graft.

The prosthesis 10 also comprises a fenestration supporting stent 50, aligned longitudinally with the fenestration 44. The fenestration supporting stent 50 has a plurality of proximal apices 51 and a plurality of distal apices 53, the proximal and distal apices being connected to each other by a plurality of stent struts 55 extending therebetween, as shown in FIGS. 2, 3, 5, 11 and 12. The fenestration 44 is provided between two struts 55 of the fenestration supporting stent 50, the combination of two struts 55 and a distal apex 53 of the fenestration supporting stent 50 defining two sides 78, 82 and the distal end 84 of the fenestration.

The fenestration supporting stent 50 thereby partially surrounds and supports the fenestration 44. In particular, a distal apex 53 and two Neighboring struts 55 of the fenestration supporting stent 50 form two sides 78, 82 and the distal apex at the distal end 84 of the triangular fenestration 44. A pair of proximal apices 53 of the fenestration supporting stent 50 coincide with the corners 86, 88 at the proximal end of the fenestration 44. It is noted that, in this embodiment, there is not an additional support at the proximal side 80. However, it is not excluded that in other embodiments a support member can be provided across the proximal side 66 to further support the proximal side 80. The fenestration supporting stent 50 in this embodiment is positioned internally of the graft material, but in other embodiments it can be external.

The distal apices 53 of the fenestration supporting stent 50 have larger radii of curvature than the proximal apices 51. In particular, the distal apices 53 all have a radius of curvature which matches the curvature of the distal corner 84 of the triangular fenestration 44. In some embodiments, not all of the distal apices 53 need have a larger radius of curvature than the proximal apices 51, but at least the fenestration-supporting apex of the fenestration-supporting stent ring is formed by a distal apex 53 having a larger radius of curvature than the proximal apices 51 of the fenestration supporting stent 50. In this embodiment, the distal apices 53 have a radius of curvature of 3.75 mm and the proximal apices 76 have a radius of curvature of 0.75 mm. Other embodiments can have different radii of curvature. Preferred ranges are 2 mm to 4.5 mm for the distal apices and 0.5 mm to 1.5 mm for the proximal apices.

The larger radius of curvature of the distal apices 53 of the fenestration supporting stent 50 creates a large fenestration area, improving the ability of the stent 50 to accommodate a branch extension graft inserted therethrough without constricting or impeding the graft.

Figure 5:
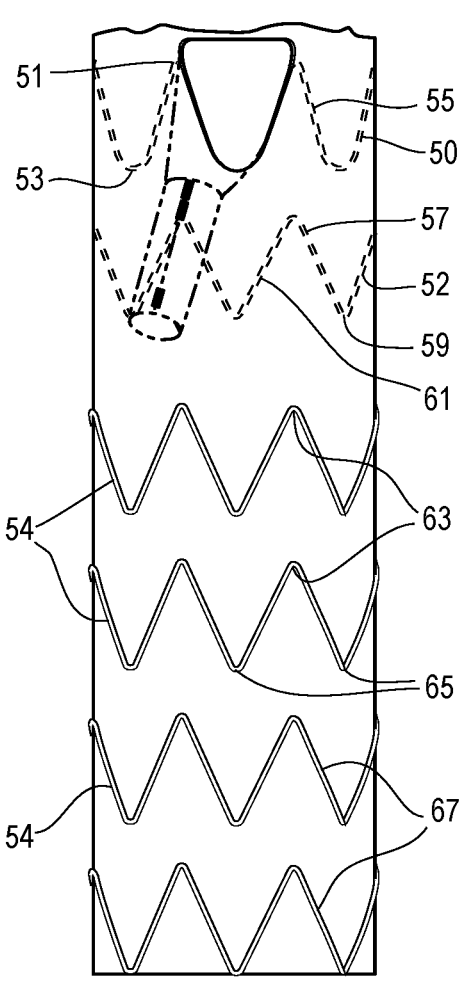
FIG. 5 is a partial and enlarged front view of a prosthesis such as stent graft.

The prosthesis 10 also includes an auxiliary stent 52, located distally of the fenestration supporting stent 50. The auxiliary stent 52 is a regular zig-zag stent, having a set of proximal apices 57 and a set of distal apices 59 which are connected by struts 61, as shown in FIG. 5.

The prosthesis 10 also includes a series of external body stents 54, distributed along a distal portion of the tubular graft body 12, between the auxiliary stent 52 and the distal end 20. The body stents 54 are regular zig-zag stents, each having a set of proximal apices 63 and a set of distal apices 65 which are connected by struts 67, as shown in FIG. 5. Unlike the other stents of the prosthesis 10 shown, the body stents 90 are in this embodiment disposed on the outside of the tubular graft body 12, although they can in other embodiments be internal or disposed within the thickness of the graft material. The body stents 54 are spaced equally apart from one another and circumferentially aligned, that is to say in phase, with one another. In the embodiment shown in FIGS. 2, and 3, and 5, there are four body stents 54, 23 positioned so that the distal apices 65 of one stent are offset 7 mm longitudinally from the proximal apices 63 of the next. In other embodiments, there could be any number of body stents 54 and the spacing between them could be any suitable distance. The distalmost of the body stents 54 is disposed at the distal end 20 of the tubular graft body 12 so that its distal apices 65 extend to a distal edge of the graft material.

In FIG. 3, the proximal and distal sets of apices of the first proximal sealing stent 22 (excluding the scallop apices), nested stent 48, and fenestration supporting stent 50 are each arranged in a plane that is angled from a perpendicular cross-section of the tubular graft body 12 (in other words angled relative to the distal end 20). This creates a slanted alignment of the sets of apices of each stent in the tubular graft body 12 when viewed in profile, as shown in FIG. 3.

The set of body apices 34 of the first proximal sealing stent 22, in particular, is arranged at an angle relative to the distal end 20 such that the apices 34 are aligned on a slant which matches the tapered end of the tubular graft body 12. This further enables the prosthesis 10 to accommodate the curvature of the vessel, so that the first proximal sealing stent 22 acts against the vessel wall at a desired angle in the curvature and thereby provides an improved seal. Because of the wedge-shape of the first proximal sealing stent 22 in this embodiment, the distal apices 30 are arranged at an angle which is relatively shallower than that of the body apices 34.

The proximal and distal sets of apices 72, 72 of the nested stent 48 are arranged at an angle which matches that of the distal apices 30 of the first proximal sealing stent 22. The proximal and distal sets of apices 51, 53 of the fenestration supporting stent 50 are arranged at an angle which is relatively steeper than that of the apices of the nested stent 48. This creates a greater spacing between the fenestration supporting stent 50 and the nested stent 48 circumferentially opposite the scallop (in other words, at the inner curve region 62) than nearest the scallop. This is beneficial to allow for the curvature of the prosthesis without interference between the stents at the inner curve region.

It should be appreciated that the struts of the stents that are angled in this way are not angled internally into the lumen 2 (that is, they remain flush with the sidewall 14 of the tubular graft body 12). Where an optimal seal is achieved, the internal lumen 16 of the prosthesis 10 will exactly align with the vessel. In other embodiments of the prosthesis 10, any combination of the stents could be angled in this way. Some embodiments have no stents that are slanted or angled in this way. Shown partially in FIGS. 6 and 7, the prosthesis 10 of the described embodiments is combined with an introducer 100 configured for deployment of the prosthesis 10 in a curved lumen, whereby the prosthesis is mounted on the introducer in a compressed condition such that the inner curve region 62 is arranged to be deployed on the inside of the curve of the lumen. The introducer 100 in these embodiments may include a pre-curved cannula (not shown), although this is not essential. One suitable pre-curved cannula is disclosed and described in U.S. Pat. No. 9,198,787 to Kratzberg, et al. ("Conformable prosthesis delivery system and method for deployment thereof"), issued on Dec. 1, 2015, the disclosure of which is incorporated by reference herein in its entirety. The wedge shaped first proximal sealing stent 22 is mounted on the introducer so that the narrow end of the wedge shape is arranged to be deployed on the interior of the curve of the vessel, thereby providing accurate orientation in the vessel.

Returning to FIGS. 1, 6, 7 and 10, the prosthesis 10 of the described embodiments make also include one or more conformance ties 43. The conformance ties 43 are disposed circumferentially around the first proximal sealing stent 22 and are operable to contract the first proximal sealing stent 22 radially onto the introducer, where they are held by a release wire (not shown) to releasably maintain this constricted configuration.

Suitable conformance ties are disclosed and described in EP4026518 and US Publication NO. 2022/0211482 ("Stent Graft") to Schmidt, et al, the disclosure of which is incorporated by reference in its entirety and described below.

The conformance ties 43 may comprise a loop arrangement to reduce the diameter around the distal end of the first proximal sealing stent 22 to lead to an angled position or conical configuration of the proximal stent. The diameter reducing loop arrangement comprises first and second loop elements.

The first loop element may include a first end and a second end, and a strand section between the first and second ends. The first loop element includes a loop at the second end. In the embodiment shown in the figures, the first loop element consists of a single strand which passes from the first end to the second end, where it loops back on itself to the first end, thereby forming a loop at the second end. In this way, the first loop element includes a first strand section from the first end to the second end of the first loop element and a second strand section from the second end to the first end of the first loop element. However, in other embodiments, the first loop element can include a loop at the second end without the strand section necessarily being part of a single strand which loops all the way back to the first end. For example, the strand can be tied to itself at a point between the first and second ends, for example by the second strand section extending from the second end and being tied to the first strand section between the first and second ends of the first loop element.

The first end of the first loop element is attached at a distal end of the first proximal sealing stent 22, in this embodiment to a distal part of the first proximal sealing stent 22, although in other embodiments it can be attached to the tubular graft body 12. In the embodiment shown in the figures, the first end of the first loop element is tied to the first proximal sealing stent 22 with a knot at a first distal apex 30 of the first proximal sealing stent 22. Furthermore, in the embodiment shown in the figures, owing to the fact that the strand of the first loop element loops all the way back to the first end, both ends of the strand are tied to the first proximal sealing stent 22 at the first distal apex 30 of the first proximal sealing stent 22. In particular, the first end of the first loop element, and therefore both ends of the strand of the first loop element, are tied to a strut 40 of the first proximal sealing stent 22 at the first distal apex 30.

The second loop element includes a first end and a second end, and a strand section between the first and second ends. The second loop element is similar to the first loop element already described. The second loop element is attached at the distal end of the first proximal sealing stent 22, in this embodiment to a distal part of the proximal stent in the same manner as described above for the first loop element, although, as for the first loop element, in other embodiments the first end of the second loop element can be attached to the tubular graft body 12. In the embodiment shown in the figures the second loop element is attached at the first distal apex 30, which is the same apex to which the first end of the first loop element is attached. In other embodiments, it is possible for the first ends of the first and second loop elements to be attached at different apices, but this would provide less effective diameter restriction.

The first and second loop elements, in particular the first and second strand sections thereof, are configured to pass or be wrapped circumferentially around the distal end of the proximal stent in opposite directions from the respective first ends such that the second ends of the first and second loop elements can meet in a constricting configuration. The constricting configuration can restrict the diameter of the distal end of the proximal stent.

The second ends can be retained by a release wire (not shown) in the constricting configuration to maintain a constricted diameter at the distal end of the proximal stent. In the embodiment shown in the figures, the first and second loop elements, in particular the strand sections thereof, are between them configured to pass around the entire circumference of the tubular graft body 12 at the distal end of the first proximal sealing stent 22 in the constricting configuration. Each of the first and second loop elements is configured to pass circumferentially around a part of the circumference of the tubular graft body 12 at the distal end of the first proximal sealing stent 22 in the constricting configuration. In the embodiment shown, the release wire and first and second loops meet at a point longitudinally aligned with (that is, at the same position circumferentially as) the scallop 32 and fenestration 44.

In the embodiment shown in the figures, the first and second loop elements, in particular the strand sections thereof, pass circumferentially around the distal end of the first proximal sealing stent 22 in opposite directions, and overlap each distal apex 30 which they pass such that between them they overlap every distal apex 30 of the proximal stent in the constricting configuration.

The size of the loop elements determine the size of the diameter reduction of the distal end of the first proximal sealing stent 22 in the constricting configuration and the angle of the conical shape created. The lengths of the loop elements may vary depending on the (expanded) diameter of the prosthesis 1.

In the embodiment shown in the figures, in the constricting configuration the first and second loop elements pass circumferentially around the distal end of the first proximal sealing stent 22 in opposite directions, and the strand sections thereof are attached to the tubular graft body 12 and/or the first proximal sealing stent 22 at a majority of the respective distal apices 30 of the proximal stent which they pass. In other words, at a majority of the distal apices 30 of the first proximal sealing stent 22, the proximal stent and/or the graft body is attached to one or other of the first and second loop elements. The number of distal apices at which the strand sections are attached is enough to allow the strand sections to contract the stent without slipping down. In the embodiment shown in the figures, the strand sections of the loop elements are attached to the graft body by penetrating the graft material at the respective apices.

The attachment of the strand sections of the first and second loop elements to the tubular graft body 12 and/or the first proximal sealing stent 22 at distal apices 30 of the proximal stent can serve to control the loop elements to prevent them sliding off the distal end of the proximal stent and to make sure the loop elements do not get caught when released. Furthermore, as a result of their attachment to the tubular graft body 12 at distal apices 30 of the first proximal sealing stent 22, the loop elements can only slide in the direction around the graft and not along the length of the graft.

In the embodiment shown in the figures, in the constricting configuration each of the first and second loop elements passes a set of distal apices 30 of the first proximal sealing stent 22 and is attached to the tubular graft body 12 at a majority of the distal apices of the respective set by the loop element, in particular the strand sections thereof, weaving through the graft material at each of those distal apices. In the embodiment shown in the figures, at each of the distal apices at which it is attached to the graft body, the first and second strand sections of the respective loop element penetrate the tubular graft body 12 and pass from external of the tubular graft body 12 to internal of the tubular graft body 12, pass around one of the struts 24 of the first proximal sealing stent 22 at the distal apex and then pass from internal of the tubular graft body 12 to external of the tubular graft body 12. In other words, the strand sections of the loop elements pass radially internally of the tubular graft body 12 around one of the two struts 24 at a majority of the distal apices of the respective set of distal apices 30 of the first proximal sealing stent 22 but otherwise pass circumferentially around the tubular graft body 12 externally to the tubular graft body 12. Nevertheless, it is possible in other embodiments for the loop elements to be attached to the proximal stent and/or the tubular graft body 12 in a different manner.

As can be seen, in the embodiment shown in the figures, each of the first and second loop elements is attached to the graft body and/or proximal stent only at the distal end of the proximal stent.

Of course, in embodiments in which the second strand section does not pass all the way back to the first end of the respective loop element, it may be only the first strand section which passes circumferentially around the distal end of the proximal stent and is attached to the graft body and/or proximal stent.

In some embodiments, it is possible for the loop elements to be substantially unattached to the graft body or proximal stent except at their first ends. However, this is not preferred for the reasons discussed. Furthermore, although in the embodiment shown in the figures the first and second strand sections of each loop element are attached to the graft body and/or the proximal stent at a majority of the distal apices of the proximal stent which they pass, in other embodiments just one or other of the strand sections can be so attached. Furthermore, it is not excluded that the first and/or second strand section of the first and/or second loop element can be attached to the proximal stent and/or graft body at a plurality of locations around the circumference of the graft body other than at distal apices of the proximal stent. However, attachment at distal apices is preferable for efficient constriction of the distal end of the proximal stent.

In the constricting configuration, the first and second loop elements together extend around the entire circumference of the tubular graft body 12 and distal end of the first proximal sealing stent 22 and the first loop element passes through the loop at the second end of the second loop element, allowing for a release wire to pass through the loop at the second end of the first loop element to hold the first and second loop elements in the constricting configuration. Owing to the location of the first and second loop elements around the distal end of the proximal stent, the diameter reducing loop arrangement is configured to constrict the distal apices of the proximal stent and cause the proximal stent to adopt a substantially conical or frustoconical shape. This conical or frustoconical shape allows the proximal sealing stent to deploy in a more angular position, which leads to a better conformance to the aortic curve.

In the embodiment shown in the figures the first and second loop elements are made from thread which is green braided PTFE impregnated polyester fibre suture. Other materials can be used in other embodiments; however, the first and second loop elements are preferably each provided by a suture and most preferably by a single strand thereof.

In the embodiment shown in the figures, only the first proximal sealing stent 22 is encircled with conformance ties 43. However, in other embodiments, one or more of the other stents may have diameter-reducing ties. The distalmost stent may optionally have a conventional retention arrangement configured to be released in a conventional manner. However, this is not critical and details are therefore not described herein.

In use, a release wire (not shown) is passed through the loop at the second end of the first loop element, externally to the tubular graft body 12. As a result, both the loop elements are attached to the release wire and each other. They are held by the release wire in the constricting configuration which pulls the distal apices of the proximal stent radially inwardly and holds the sealing stent in a substantially conical or frustoconical shape, in particular a proximally facing conical or frustoconical shape. The diameter reducing loop arrangement can be released from the constricting configuration by pulling the release wire, which releases the first and second loop elements from each other and allows their respective second ends to separate. As a result, the loop elements no longer constrict the diameter of the distal end of the first proximal sealing stent 22, which is consequently free to expand.

It is also noted that the release wire passes through the loop at the second end of the first loop element but not the loop at the second end of the second loop element. In other embodiments, it can pass through the loops at the second ends of both the first and second loop elements. The conformance ties can have any features described in EP4026518 and US Publication NO. 2022/0211482 ("Stent Graft") to Schmidt, et al, the disclosure of which is incorporated by reference in its entirety.

After being released from the introducer, the prosthesis 10 is partially deployed, whereby the first proximal sealing stent 22 is held in a reduced diameter configuration by the conformance ties 43, as shown in FIG. 6. The partially deployed configuration enables a clinician to reorient and align the prosthesis 10 in the vessel before full deployment. FIG. 6 shows an exemplary alignment of the prosthesis 10 in a simulated aortic arch: the proximal end 18 of the tubular graft body 12 is distal of the brachiocephalic trunk (BT), the generally straight distal portion of the scallop 32 is aligned between the openings of the left common carotid artery (LCC) and the left subclavian artery (LSA), and the fenestration 44 is aligned with the left subclavian artery (LSA). Once the clinician has positioned the prosthesis 10 as desired, the conformance ties 43 can be released (using a release wire as described above) to initiate the full deployment of the prosthesis 10, allowing the first proximal sealing stent 22 to expand to engage the wall of the vessel. This deployed state can be seen in FIG. 7. In the embodiments shown, the prosthesis 10 is designed to deploy into a 38 mm diameter vessel, the prosthesis 10 having a fully expanded diameter of 42 mm and being contractible into a 22 Fr (7.33 mm) diameter sheath. These dimensions can be tailored to the target vessel. Other embodiments can have any suitable diameters.

It is to be noted that the particular conformance ties described in detail above are not necessary in every embodiment. It is also to be noted that other arrangements for constricting the first proximal sealing stent 22 can be used in some embodiments. Another suitable conformance system is disclosed and described in U.S. Pat. No. 9,855,128, to Kolbel, et al., ("Introducer for Deploying a Stent Graft in a Curved Lumen and Stent Graft Thererfor,") issued on Jan. 2, 2018, the disclosure of which is incorporated by reference herein in its entirety.

A method of placing the prosthesis 10 in a lumen of a patient includes inserting the prosthesis 10 into the lumen of the patient endovascularly (typically from a femoral approach) and deploying the prosthesis. The lumen may be curved, in which case the prosthesis 10 is deployed so that the inner curve region is on the inside of the curve of the lumen.

The lumen will typically be in the vasculature of the patient. The embodiment of the prosthesis as shown in the figures is designed for implantation into the aortic arch, between the ascending and descending aorta. A method of placing the prosthesis 10 into the aortic arch includes: inserting the prosthesis 10, using an introducer as described above, into the vasculature of the patient; orienting the prosthesis 10 in the lumen of the aortic arch, with the inner curve region on the inside of the curve of the lumen; and, deploying the prosthesis 10 so that: the first proximal sealing stent 22 deploys substantially perpendicularly to the curve of the lumen; a distal end of the scallop 32 is aligned between the subclavian and carotid arteries; and the fenestration 44 is aligned with a junction of the left subclavian artery.

Advantages include that the prosthesis can accommodate the curvature of the aortic arch, while making sure that the stent does not harm the vessels in the curvature, supporting the left subclavian artery (LSA), and having a minimum 10-15 mm proximal sealing zone. The prosthesis can also be deployed with the sealing stent (first proximal sealing stent 22) properly aligned to the perpendicular to the vessel at the left subclavian while sealing the prosthesis within the short length of vessel available between the subclavian and the carotid, with reduced risk of erosion to the vessel. In particular, the prosthesis can land in the small area between the subclavian and carotids, with the wedge shaped stent and tapered stent and graft end accommodating the curve of the aorta in this area and the nested stent maximising the sealing in the sealing zone.

As discussed above, the proximal stent in the preferred embodiment has a wedge shape and varying radii of curvature of apices to make sure the stent does not erode the vessel as well as enabling a 42 mm stent/stent graft able to be loaded into a 22 Fr (7.33 mm) sheath.

Although the internal branch graft 46 of the illustrated embodiments is described as having two distinct portions, in some embodiments, more than two portions may be provided. These may have longitudinal axes intersecting with the longitudinal axis of the tubular graft body 12 at acute angles that are progressively smaller, such that each portion has a longitudinal axis intersecting at a smaller acute angle than its adjacent proximal portion.

Figure 13:
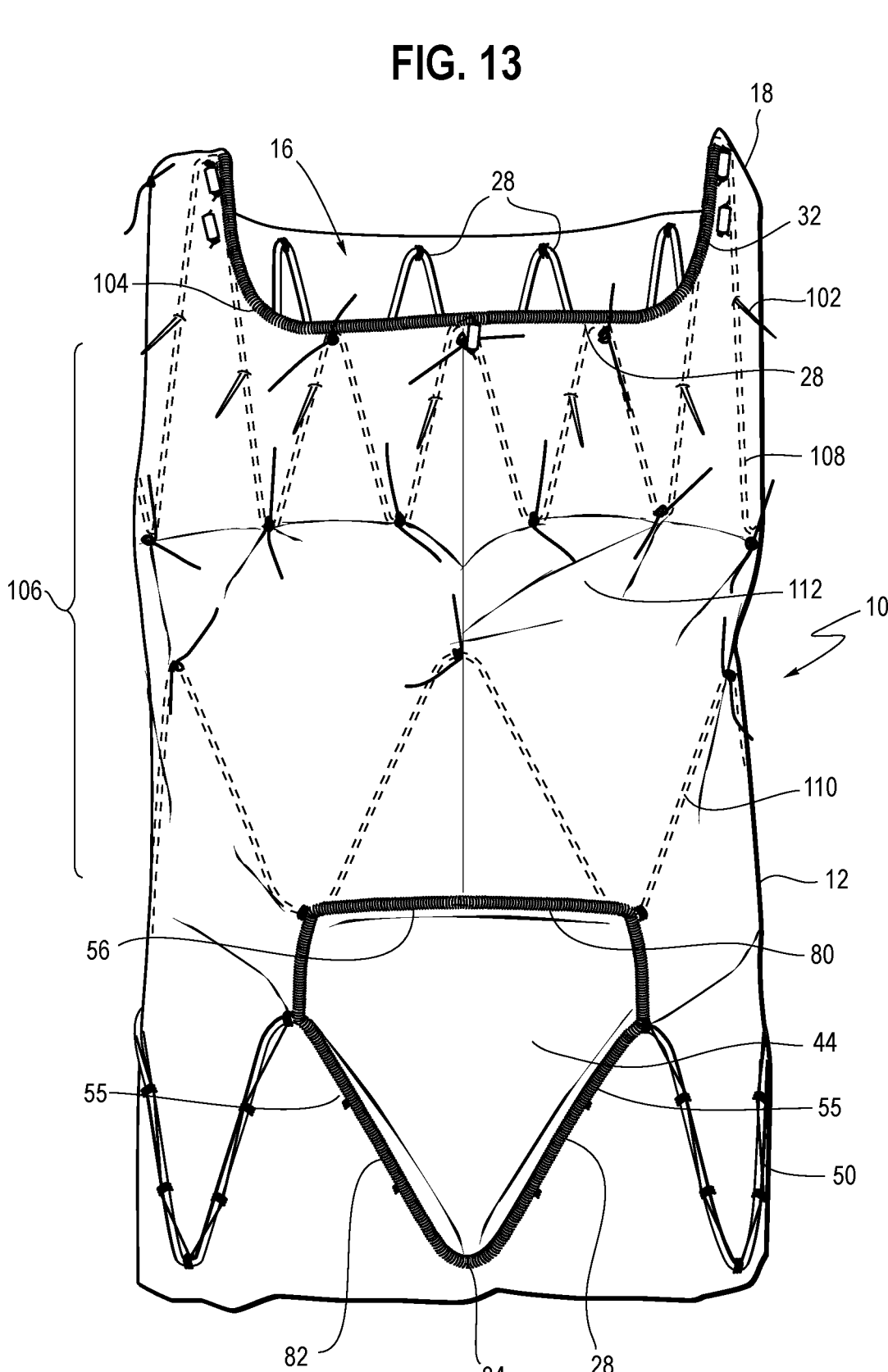
FIG. 13 shows a front view of the proximal end of another prosthesis of the invention.
Figure 14:
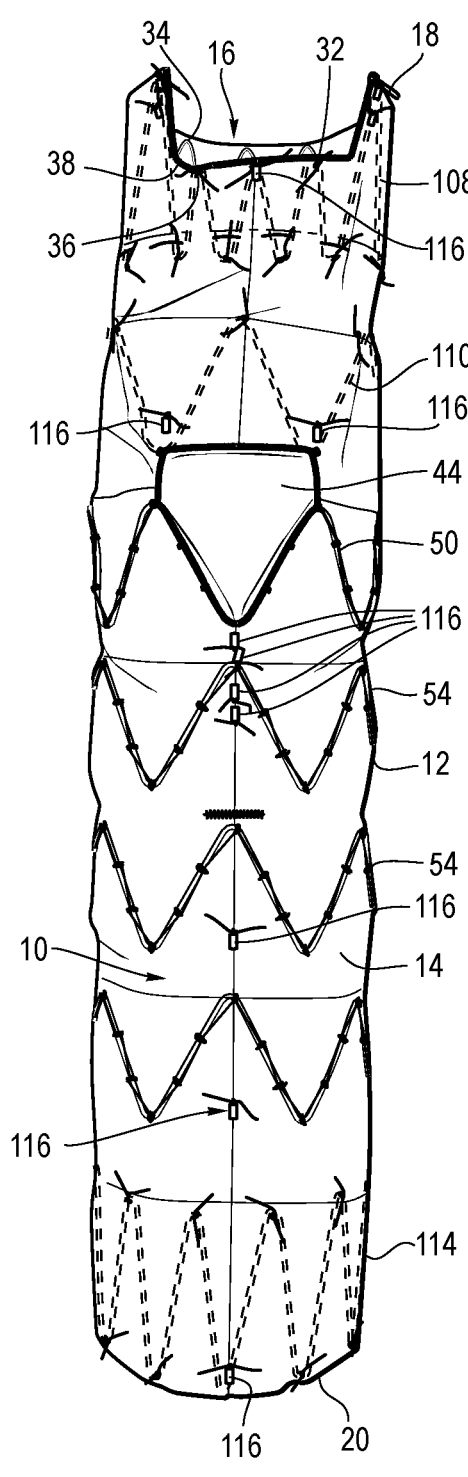
FIG. 14 shows a front view of the prosthesis of FIG. 13.
Figure 15:
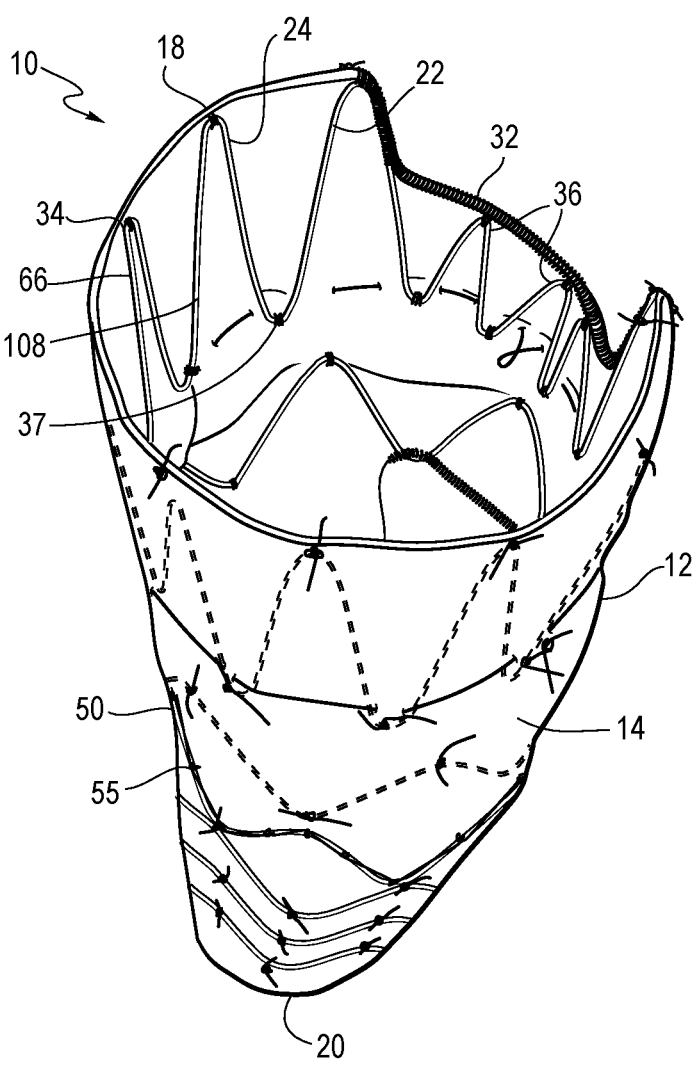
FIG. 15 shows a view from the proximal end of the prosthesis of FIGS. 13-14.

FIGS. 13 to 15 show another embodiment of a prosthesis 10, which is a stent graft for deployment in the aortic arch. Unless otherwise indicated, the features and modifications of this embodiment of prosthesis are the same as described above. However, they do not necessarily need to be.

The stent graft includes a plurality of expandable stent rings arranged along a length of tubular graft material having a proximal end and a distal end, the plurality including at least a proximal stent ring 22 at the proximal end of the tubular graft material and a distal stent ring 23 at or near the distal end of the tubular graft material, and at least one intermediate stent ring between the proximal stent ring and the distal stent ring.

The upper portion of prosthesis 10 is shown in FIG. 13. The prosthesis 10 comprises a graft in the form of a tubular graft body 12 including a sidewall 14 with an internal lumen 16 therethrough. The tubular graft body 12 has a proximal end 18 and a distal end 20 (shown in FIGS. 14 and 15)

The prosthesis 10 includes a series of stents distributed longitudinally along the tubular graft body 12. Each of the stents comprises a plurality of peaks and valleys connected in a zig-zag arrangement to form a ring around the tubular graft body 12, on the inside or outside of the tubular graft body 12, or within the tubular graft body 12 itself, with adjacent peaks and valleys being connected by struts.

A scallop 32 is located at the proximal end 18 of the tubular graft body 12 in a first circumferential region. The dimensions of the scallop 32 can be tailored according to target vessel. Barbs 102 are provided in the region of graft material in which the scallop 32 is formed. These assist in holding the prosthesis 10 in the correct location during deployment. The barbs 102 may extend distally from the struts 24 through the graft material to the exterior to engage the aortic wall to prevent movement of the prosthesis. Suitable barbs are disclosed and described in U.S. Pat. No. 7,232,459 to Greenberg, et al. ("Thoracic Aortic Aneurysm Stent Graft), issued on Jun. 3, 2004, the contents of which are incorporated by reference herein in their entirety.

The scallop 32 in this embodiment is configured to allow for a proximal sealing zone of from about 20 mm to about 40 mm and preferably about 30 mm. Scallop 32 may have a separate reinforcement wire 104 about its perimeter which is stitched to the graft material at the perimeter.

As shown in FIG. 13, the proximal sealing zone 106 includes two sealing stents 108, 110, a proximal sealing stent 108 and a distal sealing stent 110 longitudinally spaced from one another such that the proximal apices of the distal sealing stent 110 are located distally of the distal apices of the proximal sealing stent 108. There is therefore a region of unstented graft material 112 (forming a ring of unstented graft material in this embodiment) between the proximal and distal sealing stents 108, 110. In this embodiment, the longitudinal extent of the region of unstented graft material 112 is from about 3 mm to about 10 mm. The longitudinal extent of the region of unstented graft material can be at least about 3 mm, and preferably about 7 mm. Therefore, in contrast to the embodiments described above, there is no stent nested with the proximal sealing stent 108. The proximal sealing stent 108 is arranged at the proximal end 18 of the prosthesis 10. This is similar to the first proximal sealing stent 22 of the embodiments described above. The first proximal sealing stent 108 is an internal stent; in other words, it is disposed around an interior surface of the tubular graft body 12. However, in other embodiments, it can be an external stent or it can be disposed within the thickness of the graft material.

The proximal stent ring (the sealing stent 108) comprises a plurality of stent units, each stent unit comprising first and second struts connected by a proximal apex, the stent ring comprising a plurality of distal apices, each stent unit being connected to a Neighboring stent unit by a distal apex 30. The plurality of stent units includes at least one scallop unit and at least one supporting unit 39, where the proximal apex of each scallop unit is located at the scallop 32 and the proximal apex of each supporting unit 39 is located in a second circumferential region distinct from the first circumferential region; wherein the first and second struts of each of the at least one scallop unit are shorter than the first and second struts of each of the at least one supporting unit 39.

The proximal sealing stent 108 may have from about sixteen to about twenty-eight apices 26, eight to fourteen of which are proximal apices 28 and eight to fourteen of which are distal apices 30, although in practice this can be varied for example in dependence on the prosthesis diameter. In other embodiments there can be any suitable number of apices 26. For example, with a Nitinol stent, each end could have from about five to about ten apices. It is preferred that there are the same number of proximal apices 28 and distal apices 30, but it is not necessary.

The body apices 34 are all disposed at the proximal edge 56 of the graft material. It is preferred that all the body apices 34 are disposed at the proximal edge 56 of the graft material in order to most effectively seal the proximal end 18 of the tubular graft body 12. However, in other embodiments, the body apices 34 can be variously disposed further distally or proximally than shown.

In this embodiment there are three scallop apices 36. The scallop apices 36 are disposed distally of the body apices 34 that are adjacent to the scallop 32. In particular, it has been found to be beneficial that the scallop apices 36 do not extend all the way to the most proximal end of the tubular graft body 12. This arrangement reduces the stent struts and apices in the scallop 32 that might otherwise impinge upon the vessel wall at the location of the branch vessel and thereby reduces the possibility of trauma or damage to the vessel. In this manner, the first proximal sealing stent 108 can itself be said to include a scallop at its proximal end in the region of the scallop 32 in the tubular graft body 12.

The set of distal apices 30 are all disposed distally of the distal end of, in particular of a distalmost edge of, the scallop 32. It is preferred that all of the distal apices 30, or at least a majority thereof, are disposed at least longitudinally level with, or distally of, a distal end of or a distalmost point on the scallop 32, which improves the ability of the proximal sealing stent 108 to seal the full perimeter of the scallop 32. In this embodiment, the distal apices 30 are also all aligned with one another.

In the illustrated embodiment, the longitudinal positions of the distal apices 30 do not vary around the circumference of the tubular graft body 12, that is to say that the distal apices are longitudinally level. However, in some other embodiments the longitudinal positions of the distal apices 30 may vary around the circumference of the graft body, in the manner of the embodiments described above. Furthermore, in other embodiments, the distal apices can be unaligned.

The scallop apices 36 are located at the distal end of the scallop 32. As with the embodiments described above, the body apices 34 are all covered, that is to say overlapped, by graft material. In this embodiment, the apices 26 of the proximal sealing stent 108 do not extend beyond the graft material (that is to say that the proximal stent is entirely covered by graft material). The strut length is such that the scallop apices 36 are positioned distally of the proximal edge 16 and distal end of the scallop and thereby are covered by graft material. This may be particularly useful where the proximal sealing stent 108 is made of Nitinol. The scallop apices 36 are sutured to the graft material at the distal edge of the scallop 32 to hold them in position. The perimeter of the scallop is further supported by a wire stitched thereto.

In other embodiments, the scallop apices 36 may extend proximally of the proximal edge 16 of the tubular graft body 12 at the scallop 32, in other words extend proximally of the distal end of the scallop, and be uncovered by the graft material. As a result, a majority, but not all, of the first proximal sealing stent 22 is covered by graft material. Nevertheless, the graft covers at least a majority of each of the interstices between the peaks of the proximal sealing stent 108. In other words, the spaces between struts adjoining Neighboring proximal apices 36 of the proximal sealing stent 108 are each substantially or completely overlapped by graft material.

In this embodiment, the struts 24 vary in length around the circumference of the proximal sealing stent 108, creating a taller segment and a shorter segment of the stent. In particular, struts at the scallop are shorter than the struts adjacent to the scallop at each side. In other words, the first and second struts of each scallop unit are shorter than the first and second struts of each supporting unit 39.

As with the embodiment of FIGS. 1 to 7 described above, the scallop apex struts 64 of this embodiment are shorter than a majority of the body apex struts 66. In other embodiments, the scallop apex struts 64 are all shorter than any of the body apex struts 66. However, it is particularly beneficial that the scallop apex struts 64 are shorter than the body apex struts 44 that are adjacent to the scallop (in other words those in the supporting units 39 as described above). In some embodiments, the scallop apex struts 64 are shorter than just those pairs of body apex struts 66 adjacent to the scallop. In other words, it is particularly beneficial that the first and second struts of the scallop units are shorter than the first and second struts of the supporting units 39. In the embodiment shown, the scallop apex struts 64 are all the same length, but in other embodiments they can be of different lengths.

In this embodiment, the apices 26 are uniform around the circumference of the proximal sealing stent 108, in other words there is a consistent radius of curvature around the circumference, which produces uniform radial forces around the stent. In other embodiments, however, the proximal sealing stent 108 may have apices 26 having different radii of curvature around the circumference as described for the embodiments above.

In this embodiment, the proximal sealing stent 108, in contrast to the embodiment of FIGS. 1 to 7, has a proximal-distal length from a proximal end of the stent 108 to a distal end of the proximal sealing stent 108 that does not vary around the circumference of the prosthesis 10. However, in some embodiments the proximal sealing stent 108 may have a proximal-distal length from a proximal end of the stent 108 to a distal end of the proximal sealing stent 108 that varies around the circumference of the prosthesis 10.

Furthermore, in contrast to the proximal end 18 of the first proximal sealing stent 22 of the embodiment of FIGS. 1 to 7, the proximal end 18 of the proximal sealing stent 108 of the embodiment of FIGS. 13 to 15 does not have a taper. Some modifications of this embodiment may nevertheless have a taper similar to that of the embodiment of FIGS. 1 to 7.

The embodiment illustrated in FIGS. 13 to 15 does not have a slanted proximal end 18, nor a wedge-shaped proximal stent, in contrast to the embodiments described above. Nevertheless, this is not excluded and the prosthesis of FIGS. 13 to 15 can be provided with these features if desirable. As with the embodiments above, any of the other stents of the prosthesis 10 can also, or alternatively, have a wedge shape.

The second or distal sealing stent 110 may have the same fewer apices than the proximal sealing stent 108, for example, it may have from about sixteen to about twenty-eight apices 26, eight to fourteen of which are proximal apices 28 and eight to fourteen of which are distal apices 30, although in practice this can be varied for example in dependence on the prosthesis diameter. In other embodiments there can be any suitable number of apices 26. For example, with a Nitinol stent, each end could have from about five to about ten apices, and preferably five to nine apices. It is preferred that there are the same number of proximal apices 28 and distal apices 30, but it is not necessary.

As with the embodiments above, the prosthesis 10 of FIGS. 13 to 15 includes at least one fenestration provided in a side wall of the tubular graft material, the fenestration being configured for alignment with a junction of the left subclavian artery and for deployment of a side-branch therethrough; wherein the fenestration is aligned with a lumen of an internal branch graft located within the lumen of the stent graft; wherein the internal branch graft extends from the fenestration within the lumen of the stent graft.

In this embodiment the proximal end of the graft material includes first and second mutually exclusive circumferential regions. The first circumferential region including the scallop 32, which is longitudinally aligned with the fenestration 44. The triangular or trianguloid fenestration 44 is circumferentially aligned with and distal of the scallop 32. The fenestration 44 is sized and positioned so that, when the prosthesis 10 is in its fully deployed state, the fenestration 44 will accommodate the opening of a branch vessel. In the embodiment shown, the prosthesis 10 is designed to be deployed in the aortic arch, at which point, if the patient's anatomy allows, the fenestration 44 aligns with the opening of the left subclavian artery. In this embodiment the distance between the scallop 32 and the fenestration 44 is approximately 30 mm. Therefore, where a patient has a relatively large landing zone between the left common carotid artery and the left subclavian artery, this device provides for an improved seal in view of provision of the proximal and distal sealing stents 108, 110 between the scallop 32 and the fenestration 44.

The fenestration 44 may be formed by three substantially straight edges or sides as described above which are joined by three rounded corners, although in some versions there may be some longitudinal extent at the junctions between the sides of the fenestration supported by the stent and the proximal side of the fenestration. As shown in FIGS. 13-15, the fenestration 44 may be formed by a perpendicular proximal side, two angle sides and two longitudinally extending sides between the angle sides and the perpendicular proximal side.

The distal sealing stent 110 is provided adjacent to the proximal edge 66 of the fenestration 44, disposed proximally of the fenestration 44, and positioned so that its distal apices are disposed adjacent to the proximal edge 56 of the fenestration 44. In the embodiment shown, the distal apices of the distal sealing stent 110 do not extend beyond the graft material at the proximal edge 56 of the fenestration 44. Equally, the proximal edge 56 of the fenestration 44 does not extend proximally of the distal apices of the distal sealing stent 110.

The prosthesis 10 includes an internal branch graft (not shown in FIGS. 13 to 15). This may have a similar geometry and configuration as that of the above described embodiments. Other geometries and arrangements are also possible. For example, it may extend distally within the lumen 16 of the prosthesis 10, or it may extend proximally. In some embodiments, the prosthesis could comprise a fenestration but not a branch graft.

As with the embodiments described above, at least one intermediate stent ring is a fenestration-supporting stent ring, wherein the fenestration-supporting stent ring is a zig-zag stent having a plurality of proximal apices and a plurality of distal apices, the proximal and distal apices connected to each other by a plurality of stent struts 55 extending therebetween, wherein at least one of the distal apices is a fenestration-supporting apex. The fenestration 44 is thus supported by a fenestration supporting stent 50, aligned longitudinally with the fenestration 44. The fenestration 44 is provided between two struts 55 of the fenestration supporting stent 50, the combination of two struts 55 and a distal apex of the fenestration supporting stent 50 defining two sides 78, 82 and the distal end 84 of the fenestration. The fenestration supporting stent 50 in this embodiment is positioned externally of the graft material, but in other embodiments it can be internal.

In the prosthesis illustrated in FIGS. 13 to 15, the distal apices and the proximal apices of the fenestration-supporting stent all have the same radius of curvature. However, in some embodiments, the distal apices can have a larger radius of curvature than the proximal apices in a manner similar to the embodiments described above. Nevertheless, the distal apices have a radius of curvature that matches the curvature of the distal end 84 (corner) of the triangular fenestration 44.

In the embodiment of FIGS. 13 to 15, the fenestration supporting stent 50 has the same number of apices as the distal sealing stent 110. Its proximal apices are aligned in a longitudinal direction with the distal apices of the distal sealing stent 110 and its distal apices are aligned with the proximal apices of the distal sealing stent 110. However, this is not necessary. The proximal apices of the fenestration supporting stent 50 could be aligned with the proximal apices of the distal sealing stent 110.

As illustrated in FIGS. 13 and 14, the fenestration 44 has a proximal edge 56, the proximal edge including at least a portion that is substantially perpendicular to the longitudinal axis of the stent graft. The proximal edge 56 of the fenestration 44 is unobstructed from stenting, although in some embodiments a supporting wire could be provided therealong. It is preferred, however, that the proximal edge 56 of the fenestration be defined merely by suture stitching.

As with the embodiments described above, the prosthesis 10 includes a series of body stents 54. In contrast to the embodiments described above, the proximal and distal sealing stents 108, 110 and the fenestration supporting stent 50 are not angled relative to the distal end of the prosthesis 10. However, in some embodiments they can be.

As shown in FIG. 14, a distal-most stent 114 is provided at the distal end of the prosthesis 10. The distal-most stent is the softest stent in the prosthesis and provides less radial force that the other stents of the prosthesis 10. This reduces the risk of trauma. In this embodiment, the distal-most stent 108 may have may have sixteen to twenty-eight apices 26, eight to fourteen of which are proximal apices 28 and eight to fourteen of which are distal apices 30, although in practice this can be varied for example in dependence on the prosthesis diameter. Hence, there can be any suitable number of apices 26. It is preferred that there are the same number of proximal apices 28 and distal apices 30, but it is not necessary. The apices are connected by struts, and the struts are longer than the struts of the other stents in the prosthesis 10.

Radiopaque markers 116 are provided to assist in positioning and alignment of the device during delivery. The markers may be any suitable radiopaque material including gold, platinum, tantalum and the like. As can best be seen in FIG. 14, two markers 116 arranged longitudinally are provided at the proximal end of the graft material on each side of the scallop. A further marker is provided at the midpoint of the distal edge of the scallop 32. A marker 116 is also provided at each corner of the fenestration 44. In this embodiment four markers 116 are provided at the distal apes of the fenestration in a longitudinal arrangement. Three further markers 116 lying along the same longitudinal axis are provided along the graft material. The longitudinal alignment of these markers assists in detecting twisting of the prosthesis 10 during deployment. Other suitable radiopaque markers could be incorporated in addition to or instead of the illustrated gold markers 116. In an embodiment (not illustrated), for example a metal (for example, platinum) wire or coil could be used to mark the peripheries of the scallop 32 and/or the fenestration 44. For example, a radiopaque coil could be coiled about the scallop wire, the distal struts of the fenestration support stent or other stent. In another embodiment such a marker could be placed in a V-shape to mark the distal apex 63 of the fenestration 44.

An advantage of the embodiment illustrated in FIGS. 13 to 15 is that a longer seal zone is provided between the scallop 32 and the fenestration 44. And, the arrangement of a proximal sealing stent 108 and a distal sealing stent 110 having an unstented area of graft material 112 between provides flexibility. For a patient having a relatively larger landing zone between their left common carotid artery and their left subclavian artery, a greater overall seal area is available.

However, for patients having a small landing zone the device can be implanted by firstly aligning the scallop 32 with the left common carotid artery. The fenestration 44, in this case will not be able to align with the left subclavian artery. In these cases, a bridging stent graft 118 (shown in FIG. 16) can be used to provide fluid communication between the lumen 16 of the prosthesis 10 and the left subclavian artery.

Figure 16:
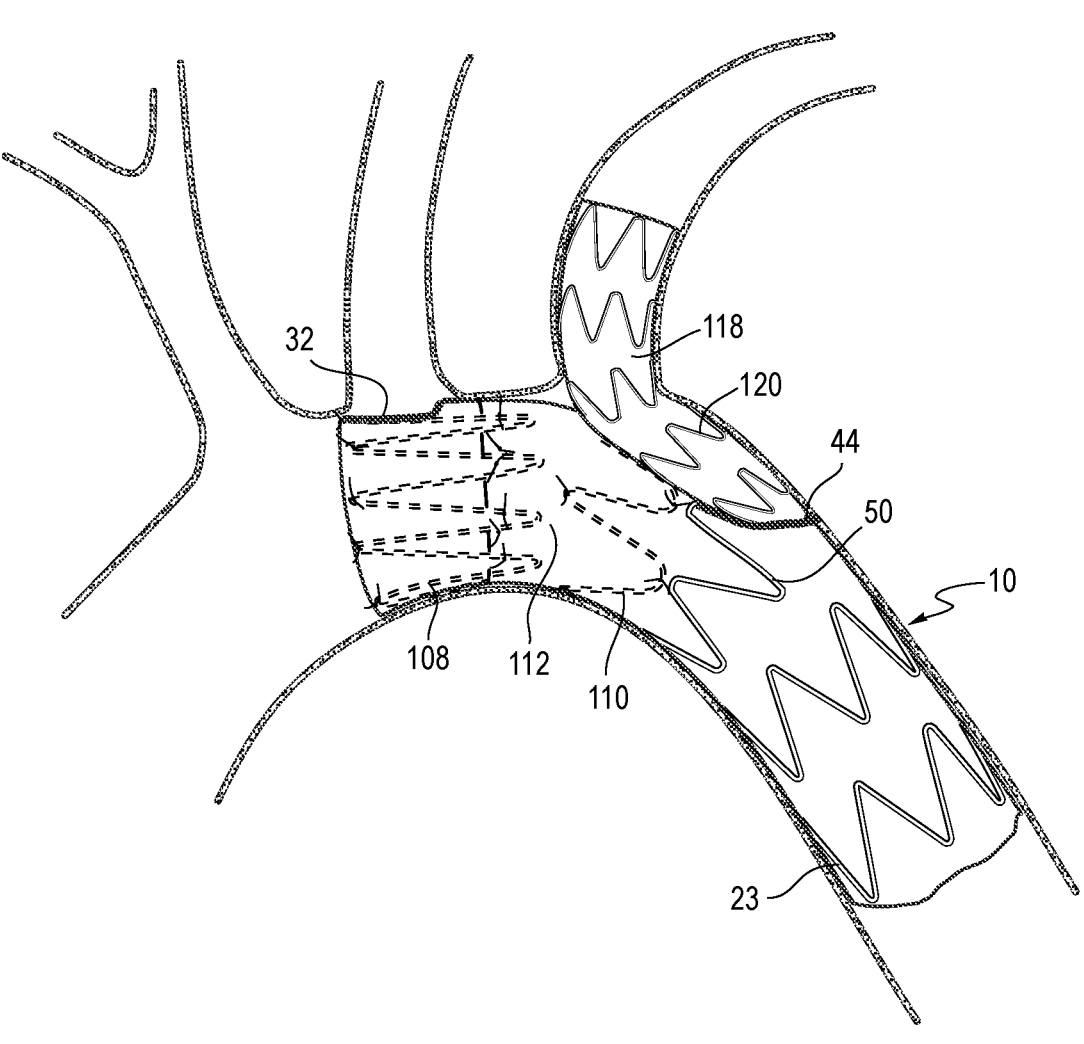
FIG. 16 illustrates the prosthesis of FIGS. 13 to 15 implanted within the aortic arch and descending thoracic aorta of a patient with a bridging stent graft bridging the left subclavian artery.

FIG. 16 schematically illustrates the prosthesis 10 located within the aortic arch of a patient having only a short (less than 30 mm) landing zone between their left common carotid artery and left subclavian artery. Features shown in this Figure are not drawn to scale. It can be seen that a good seal is maintained by the proximal sealing stent 108 at the junction between the left common carotid artery and the left subclavian artery while fluid communication between the left common carotid artery and the aortic arch is maintained via the scallop 32.

In this patient, the fenestration is unable to align with the junction of the left subclavian artery and the aortic arch and lands approximately 1-2 cm distal of the opening of the left subclavian artery. In this case, a side branch, bridging stent graft 118, is used to maintain fluid communication between the left subclavian artery and the descending aorta. The bridging stent graft 118 has a proximal end that engages within the internal branch graft 46. The bridging stent graft 118 exits the fenestration 44 and passes alongside the outside of the tubular graft body 12 of the prosthesis 10 between the distal sealing stent 110 and the vessel wall, before passing into the left subclavian artery.

At least one of the stent rings 120 of the bridging stent graft 118 has a higher radial force than the distal sealing stent 110 of the stent graft. This enables the bridging stent graft 118 to overcome the radial force of the distal sealing stent 110 and maintain an open lumen and thus a fluid connection to the left subclavian artery as it runs alongside the prosthesis 10.

With this arrangement, a good seal is maintained by the proximal sealing stent 108. A good seal is furthermore maintained by the distal sealing stent 110, which engages with the majority of the circumference of the vessel wall but for where the bridging stent graft 118 runs adjacent. Nevertheless, the combination of the distal sealing stent and the bridging stent 118 provides a good seal within the aorta. The unstented area of graft material 112 provides some flexibility allowing the distal sealing stent 110 to be pushed away from the vessel wall by the bridging stent graft 118 without dislodging the proximal sealing stent 108. In this way, the proximal sealing stent 108 is able to maintain a good seal between the prosthesis 10 and the small area available for sealing between the left common carotid artery and the left subclavian artery.

The stent graft of FIGS. 13 to 15, whether or not used with the bridging stent 118, can be delivered using any suitable deployment system, such as that described herein or that described in co-pending U.S. patent application 63/581,548, the entire contents of which are incorporated herein by reference.

The embodiment of FIGS. 13 to 15 therefore provides a device that can be used with a greater range of patient anatomies. Where a patient has a longer landing zone between the left common carotid artery and the left subclavian artery the fenestration may align with the left subclavian artery in a manner similar to the embodiment of FIGS. 1 to 7. However, this device may also be used with patients having a shorter landing zone since the fenestration 44 does not have to align with the left subclavian artery but can be fluidly connected thereto by the bridging stent 118. This device is therefore useful for a greater number of patients.

All optional and preferred features and modifications of the described embodiments and dependent claims are usable in all aspects of the invention taught herein. Further, the individual features of the dependent claims, as well as all optional and preferred features and modifications of the described embodiments, are combinable and interchangeable with one another.

In this regard as described above, an endoluminally implantable medical device is disclosed that includes a graft having a proximal end and a distal end, the proximal end including first and second circumferential regions, the first circumferential region having a scallop; and a stent disposed at the proximal end of the graft, the stent comprising a plurality of stent units including first and second stent units, each stent unit comprising first and second struts connected by a proximal apex; wherein the proximal apex of the first stent unit is more rounded than the proximal apex of the second stent unit; wherein the plurality of stent units includes at least one scallop unit and at least one body unit, wherein each scallop unit has a proximal apex located at the scallop and each body unit has a proximal apex located in the second circumferential region; wherein the first stent unit is a scallop unit of the at least one scallop unit and the second stent unit is a body unit of the at least one body unit. It is preferred that the plurality of stent units includes at least one supporting unit having a proximal apex located in the second circumferential region, and the first and second struts of each of the at least one scallop unit are shorter than the first and second struts of each of the at least one supporting unit. Preferably, the second stent unit is diametrically opposite the first stent unit. The proximal apex of each of the at least one scallop unit may be disposed proximally of a distal end of the scallop and uncovered by graft material.

The present disclosure also provides an endoluminally implantable medical device, including a graft having a proximal end and a distal end, the proximal end including first and second circumferential regions, the first circumferential region having a scallop; a stent disposed at the proximal end of the graft, the stent comprising a plurality of stent units, each stent unit comprising first and second struts connected by a proximal apex; wherein the plurality of stent units includes at least one scallop unit and at least one supporting unit, where the proximal apex of each scallop unit is located at the scallop and the proximal apex of each supporting unit is located in the second circumferential region; the first and second struts of each of the at least one scallop unit are shorter than the first and second struts of each of the at least one supporting unit; and the proximal apex of each of the at least one scallop unit is disposed proximally of a distal end of the scallop and uncovered by graft material.

It is preferred that at least one scallop unit has a proximal apex which is more rounded than the proximal apex of each of the at least one supporting unit. The plurality of stent units may include at least one supporting unit having a proximal apex located in the second circumferential region and each of the at least one supporting unit supports the scallop. Also, preferably, the plurality of stent units includes at least one supporting unit having a proximal apex located in the second circumferential region and each of the at least one supporting unit is adjacent to the scallop, wherein optionally the at least one supporting unit includes a supporting unit disposed on each side of the scallop.

The plurality of stent units may include at least one supporting unit having a proximal apex located in the second circumferential region and the proximal apex of each of the at least one scallop unit is disposed distally of the proximal apex of each of the at least one supporting unit. Preferably, the proximal apex of each scallop unit is more rounded than the proximal apex of a diametrically opposite body unit. The proximal apex of each scallop unit is preferably more rounded than the proximal apex of each supporting unit. In some embodiments, the proximal apex of each scallop unit is more rounded than the proximal apex of each supporting unit and the proximal apex of each body unit.

The plurality of stent units may include at least one supporting unit having a proximal apex located in the second circumferential region and the proximal apex of each of the at least one supporting unit is overlapped by graft material. Further, the proximal apex of each of the at least one supporting unit is preferably disposed at a proximal edge of the graft. At least a majority of each of the at least one scallop unit is preferably overlapped by graft material. Further, the proximal apex of each scallop unit is in the first circumferential region. In embodiments, the proximal apex of each scallop unit is at a distal end of the scallop.

The stent of the device according to any preceding statement can further comprise a plurality of distal apices, each stent unit of the stent being connected to a neighboring stent unit by a distal apex. It is preferred that a plurality of the distal apices are located in the second circumferential region and are disposed longitudinally level with or distally of a distal end of the scallop. Further, it is preferable that at least a majority of the distal apices of the stent are disposed longitudinally level with or distally of the distal end of the scallop. In some embodiments, all of the distal apices of the stent are disposed longitudinally level with or distally of the distal end of the scallop. It is also preferred that the distal apices of the stent are substantially aligned with one another.

The proximal apex of each of the at least one scallop unit is preferably more rounded than each distal apex of the stent in the first circumferential region. In some embodiments, the proximal apex of each scallop unit is more rounded than each of the distal apices of the stent. Optionally, the distal set of apices of the stent all have the same radius of curvature. In some embodiments, all the apices of the stent that are located in the second circumferential region have the same radius of curvature. The apices of the stent that are more rounded may have a greater radius of curvature.

The first and second circumferential regions may make up a complete circumference of the graft. The first circumferential region may be coterminous with the scallop. Preferably, at least a majority of the stent is overlapped by graft material. Preferably, each of the at least one supporting unit is completely covered by graft material. One or more of the at least one scallop unit may be partially overlapped by graft material.

There is also provided an endoluminally implantable medical device, including a graft having a proximal end and a distal end, the proximal end including first and second circumferential regions, the first circumferential region having a scallop; a stent disposed at the proximal end of the graft, the stent comprising a plurality of stent units, each stent unit comprising first and second struts connected by a proximal apex; wherein the plurality of stent units includes a plurality of scallop units and at least one body unit, wherein each scallop unit has a proximal apex located at the scallop and each body unit has a proximal apex located in the second circumferential region. The endoluminally implantable medical device can incorporate any of the optional features disclosed here. In some embodiments, the endoluminally implantable medical device of any preceding statement is configured for implantation into a curved lumen.

The stent is a first stent and has a length from a first end to a second end, the first end being the proximal end and the second end being the distal end, wherein the length of the first stent increases in both circumferential directions from an inner curve region of the device and provides the first stent with a wedge shape. The inner curve region is configured to be deployed on the inside of a curve of a lumen.

The graft may be a tubular graft and the stent is around the graft. In some embodiments, the first end of the first stent is adjacent to the first end of the graft. The proximal end of the graft may be slanted with respect to a sidewall of the graft and form an obtuse angle with respect to the sidewall at the inner curve region. Preferably, the inner curve region of the device is substantially diametrically opposite the scallop. The device has a first stent. The first stent may be an end most stent disposed at the proximal end of the graft. It may be that at least a majority of the first stent is covered by graft material. The first stent may be the stent of any preceding statement. The device may include a second stent adjacent to and distal of the first stent. Each of the first and second stents may include a plurality of proximal peaks and distal valleys, adjacent peaks and valleys being connected by struts. The peaks of the first stent may be provided by the stent units recited above. In other words, within each stent adjacent peaks and valleys are connected by struts. The graft may cover at least a majority of each of a plurality of interstices between peaks of the first stent. A strut of the second stent may be shorter than a strut of the first stent. A peak of the second stent may be nested between valleys of the first stent. Additionally, the device may comprise any of the optional features of disclosed and described below.

There is also provided an implantable medical device configured for implantation into a curved lumen, the device including a tubular graft and a first stent around the graft; the graft having a first end, a second end and a sidewall; the first stent having a length from a first end to a second end, the first end of the first stent being adjacent to the first end of the graft, the length of the first stent increasing in both circumferential directions from an inner curve region of the device and providing the first stent with a wedge shape; wherein the first end of the graft is slanted with respect to the sidewall and forms an obtuse angle with respect to the sidewall at the inner curve region; wherein the inner curve region is configured to be deployed on the inside of a curve of a lumen. It is preferred that the first end of the graft aligns with the first end of the first stent around at least a majority of a circumference of the first end of the graft.

The first end of the graft is preferably substantially equidistant from the first end of the first stent around at least a majority of a circumference of the first end of the graft. In some embodiments, the device has a proximal end and a distal end, and the first end of the stent has a taper such that the longitudinal location of the first end of the stent increases in a proximal-distal direction in both circumferential directions from the inner curve region of the device. Preferably, the first stent includes a plurality of apices at the first end thereof, wherein the taper comprises, in each circumferential direction from the inner curve region, at least three apices at the first end of the first stent offset from each other in the proximal-distal direction. Preferably, the at least three apices are adjacent apices. The taper is preferably linear. The taper provides an offset of from about 5 mm to about 20 mm, more preferably from about 10 mm to about 20 mm, more preferably from about 13 to about 17 mm, most preferably of about 15 mm. The first end of the graft preferably has substantially the same taper as the first end of the stent. In embodiments of the device according to any preceding statement, it is particularly advantageous for the taper to be configured so that the first end of the first stent deploys substantially perpendicular to the curve of the lumen.

The first end of the graft can be configured so that the first end of the graft deploys substantially perpendicular to the curve of the lumen. The first stent may be an internal stent around an interior of the graft. The first end of the graft is the proximal end of the graft, the first end of the first stent is the proximal end of the first stent, the second end of the graft is the distal end of the graft, and the second end of the first stent is the distal end of the first stent. The first stent can include a scallop at the first end thereof, preferably configured to be deployed on the outside of a curve of a lumen. The device according to any preceding statement can include at least one further stent spaced from the first stent.

The graft may include a scallop at the first end, preferably configured to be deployed on the outside of a curve of a lumen. The first stent may be an end most stent disposed at the first end of the graft. It may be that the first end of the graft is proximal and the second end of the graft is distal. In some embodiments, the device includes a second stent adjacent to the first stent. The second stent may be distal of the first stent. In embodiments, each of the first and second stents comprises a plurality of proximal peaks and distal valleys, adjacent peaks and valleys being connected by struts.

The graft may cover at least a majority of each of a plurality of interstices between peaks of the first stent. A peak of the second stent may be nested between valleys of the first stent. A strut of the second stent may be shorter than a strut of the first stent. In some embodiments, the first end of the graft includes first and second circumferential regions, the first circumferential region having a scallop. The scallop may be substantially diametrically opposite the inner curve region of the device. In embodiments, the first end of the graft is the proximal end and the second end of the graft is the distal end. The first stent may be disposed at the proximal end of the graft.

In embodiments, the first stent comprises a plurality of stent units including first and second stent units, each stent unit comprising first and second struts connected by a proximal apex. The proximal apex of the first stent unit may be more rounded than the proximal apex of the second stent unit. The plurality of stent units may include at least one scallop unit and at least one body unit, where each scallop unit has a proximal apex located at the scallop and each body unit has a proximal apex located in the second circumferential region. The first stent unit may be a scallop unit of the at least one scallop unit and the second stent unit may be a body unit of the at least one body unit. The plurality of stent units preferably includes at least one scallop unit and at least one supporting unit, wherein the proximal apex of each scallop unit is located at the scallop and the proximal apex of each supporting unit is located in the second circumferential region, and the first and second struts of each of the at least one scallop unit are preferably shorter than the first and second struts of each of the at least one supporting unit.

The proximal apex of each of the at least one scallop unit may be disposed proximally of a distal end of the scallop and uncovered by graft material. The plurality of stent units may include a plurality of scallop units and at least one body unit, wherein each scallop unit has a proximal apex located at the scallop and the each body unit has a proximal apex located in the second circumferential region.

Additionally, the device may comprise any of the optional features of the disclosed herein. The device may comprise any of the optional features the disclosures here wherein reference to the stent is to be taken as reference to the first stent.

There is also provided an endoluminally implantable medical device including a graft having a proximal end and a distal end; a first stent, the first stent being an end most stent disposed at the proximal end of the graft; and a second stent adjacent to the first stent; wherein each of the first and second stents comprises a plurality of proximal peaks and distal valleys, adjacent peaks and valleys being connected by struts; the graft covers at least a majority of each of a plurality of interstices between peaks of the first stent; a strut of the second stent is shorter than a strut of the first stent; and a peak of the second stent is nested between valleys of the first stent. The first and second stents may be longitudinally separated. Preferably, first and second struts adjoining the nested peak of the second stent are shorter than Neighboring first and second struts adjoining the adjacent valleys of the first stent. The second stent may be configured to produce a lower radial force than the first stent.

The graft may include a scallop at its proximal end. The graft may further include a fenestration, the fenestration being located closer to the distal end of the graft than the second stent is and disposed adjacent to the second stent. Preferably, the struts and apices of the second stent form a ring and at least a majority of the struts of the second stent are shorter than a first strut of the first stent. Preferably, the struts and apices of the first stent form a ring and every strut of the second stent is shorter than every strut of the first stent. Preferably, a plurality of peaks of the second stent are nested between valleys of the first stent. The nesting is preferably radially symmetric. Preferably, the plurality of nested peaks of the second stent includes at least first and second Neighboring peaks of the second stent each nested under a respective peak of the first stent. Preferably, at least a majority of the peaks of the second stent are nested between valleys of the first stent. More preferably, each peak of the second stent is nested between valleys of the first stent. More preferably, each peak of the second stent is nested between a respective pair of valleys of the first stent.

The first and second struts adjoining each nested peak of the second stent may be shorter than first and second struts adjoining the adjacent valleys of the first stent. The proximal end of the graft may include first and second circumferential regions, the first circumferential region having a scallop.

The first stent may include a plurality of stent units including first and second stent units, each stent unit comprising first and second struts connected by a proximal apex. Each proximal apex of the first stent may be a peak of the first stent. Each valley of the first stent may be a distal apex formed by adjoining stent units of the first stent. The proximal apex of the first stent unit may be more rounded than the proximal apex of the second stent unit.

The plurality of stent units may include at least one scallop unit and at least one body unit, wherein each scallop unit has a proximal apex located at the scallop and each body unit has a proximal apex located in the second circumferential region. The first stent unit is preferably a scallop unit of the at least one scallop unit and the second stent unit is preferably a body unit of the at least one body unit.

The plurality of stent units preferably may include at least one scallop unit and at least one supporting unit, wherein the proximal apex of each scallop unit is located at the scallop and the proximal apex of each supporting unit is located in the second circumferential region. The first and second struts of each of the at least one scallop unit are preferably shorter than the first and second struts of each of the at least one supporting unit. The proximal apex of each of the at least one scallop unit may be disposed proximally of a distal end of the scallop and uncovered by graft material. The plurality of stent units may include a plurality of scallop units and at least one body unit, wherein each scallop unit has a proximal apex located at the scallop and each body unit has a proximal apex located in the second circumferential region.

The device may configured for implantation into a curved lumen. In embodiments, the graft is a tubular graft. The device may include a first stent around the graft. The first stent may be the first stent according to any preceding statement. The first stent may have a length from a first end to a second end, wherein the length of the first stent increases in both circumferential directions from an inner curve region of the device and provides the first stent with a wedge shape. The first end of the first stent may be adjacent to the proximal end of the graft.

The proximal end of the graft may be slanted with respect to a sidewall of the graft. The proximal end of the graft may form an obtuse angle with respect to the sidewall at the inner curve region. The inner curve region of the device may be configured to be deployed on the inside of a curve of a lumen.

The device of any preceding aspect may be referred to as a stent graft. The graft is in the form of a tubular graft body. In embodiments, the device is a stent graft for deployment in the aortic arch. The graft of any preceding aspect may comprise a fenestration provided in a side wall of the graft. In embodiments, the first end of the graft is proximal and the second end of the graft is distal.

The fenestration may have a proximal edge connecting proximal ends of two sides of the fenestration. The proximal edge preferably may include at least a portion that is substantially perpendicular to the longitudinal axis of the graft.

The device of any preceding aspect may comprise a plurality of expandable stent rings arranged along a length of tubular graft material of the graft. The plurality of expandable stent rings may include at least a proximal stent ring at or near a proximal end of the tubular graft material and a distal stent ring at or near a distal end of the tubular graft material, and at least one intermediate stent ring between the proximal stent ring and the distal stent ring.

The proximal stent ring may be the first stent of any preceding aspect. One of the at least one intermediate stent ring may be the second stent of any preceding aspect. The distal stent ring may be an additional stent, being the distally endmost stent of the device. The at least one intermediate stent ring may include a fenestration-supporting stent ring. The fenestration-supporting stent ring may be a zig-zag stent having a plurality of proximal apices and a plurality of distal apices, the proximal and distal apices connected to each other by a plurality of stent struts extending therebetween. In embodiments, the proximal apices of the fenestration-supporting stent ring form peaks and the distal apices of the fenestration-supporting stent ring form valleys.

At least one of the distal apices of the fenestration-supporting stent ring may be a fenestration-supporting apex. The fenestration-supporting apex preferably has a larger radius of curvature than the proximal apices of the fenestration-supporting stent ring. In a preferred embodiment, the fenestration is provided between two struts of the fenestration-supporting stent ring, the combination of two struts and the fenestration-supporting apex of the fenestration-supporting stent ring defining two sides and a distal end of the fenestration. In a particular embodiment, the fenestration is configured for alignment with a junction of the left subclavian artery and for deployment of a side-branch therethrough. The fenestration may be aligned with a lumen of an internal branch graft located within a lumen of the stent graft. The internal branch graft may extend from the fenestration within the lumen of the stent graft in a distal direction.

Additionally, the device may comprise any of the other features disclosed herein.

There is also provided a stent graft for deployment in the aortic arch including: a plurality of expandable stent rings arranged along a length of tubular graft material, the plurality including at least a proximal stent ring at or near a proximal end of the tubular graft material and a distal stent ring at or near a distal end of the tubular graft material, and at least one intermediate stent ring between the proximal stent ring and the distal stent ring; at least one fenestration provided in a side wall of the tubular graft material, the fenestration configured for alignment with a junction of the left subclavian artery and for deployment of a side-branch therethrough; wherein at least one intermediate stent ring is a fenestration-supporting stent ring, wherein the fenestration-supporting stent ring is a zig-zag stent having a plurality of proximal apices and a plurality of distal apices, the proximal and distal apices connected to each other by a plurality of stent struts extending therebetween, wherein at least one of the distal apices is a fenestration-supporting apex having a larger radius of curvature than the proximal apices; wherein at least one fenestration is provided between two struts of the fenestration-supporting stent ring, the combination of two struts and the fenestration-supporting apex of the fenestration-supporting stent ring defining two sides and the distal end of the fenestration; and wherein the fenestration has a proximal edge connecting the proximal ends of the two sides of the fenestration, the proximal edge including at least a portion that is substantially perpendicular to the longitudinal axis of the stent graft.

Preferably, a sealing stent ring is provided adjacent to the proximal edge of the fenestration. The sealing stent ring may be a zig-zag stent having proximal and distal apices, and optionally the proximal edge of the fenestration does not extend proximally of the distal apices of the sealing stent ring.

In some embodiments, only a single fenestration is provided in the side wall of the tubular graft material. The fenestration is preferably aligned with and distal of a scallop at the proximal end of the stent graft, a sealing zone being provided therebetween. The fenestration supporting stent ring may be arranged around the tubular graft material at an angle such that the fenestration-supporting apex is located proximally of the circumferentially opposite distal apices of the fenestration-supporting stent ring.

In a preferred embodiment, the tubular graft material is tapered at its proximal end, wherein the fenestration-supporting stent ring is angled in the tubular graft body at an angle that matches the angle of the taper of the proximal end of the tubular graft material.

A plurality of the distal apices may have a larger radius of curvature than the proximal apices. It may be that all of the distal apices have a larger radius of curvature than the proximal apices. Preferably, at least the fenestration-supporting apex has a radius of curvature of 2 mm to 4.5 mm, most preferably about 3.75 mm. The distal apices of the fenestration supporting stent ring may all have a radius of curvature of 2 mm to 4.5 mm, more preferably about 3.75 mm. Preferably, some or all of the proximal apices of the fenestration-supporting stent ring have a radius of curvature of 0.5 mm to 1.5 mm, most preferably about 0.75 mm.

A preferred embodiment of the stent graft may include a branch graft extending distally from the fenestration and internally of the tubular graft material. The branch graft may be angled with respect to the tubular graft material of the stent graft such that as the branch graft extends distally it also extends laterally from the fenestration. The branch graft is preferably angled by an angle in the range of 5 to 45 degrees, as measured from the central longitudinal axis of the stent graft, most preferably by an angle of about 16 degrees. Preferably, the branch graft has a proximal portion having a proximal longitudinal axis and a distal portion having a distal longitudinal axis, wherein the proximal longitudinal axis of the proximal portion intersects with a longitudinal axis of the stent graft at an acute angle, and wherein the distal longitudinal axis of the distal portion intersects with a longitudinal axis of the stent graft at an acute angle, the acute angle between the distal longitudinal axis and the longitudinal axis of the stent graft being smaller than the acute angle between the proximal longitudinal axis and the longitudinal axis of the stent graft.

In a preferred embodiment, a most proximal portion of the branch graft is generally frustoconical and a most distal portion of the branch graft is cylindrical. The most proximal portion of the branch graft may be the proximal portion recited above and the most distal portion of the branch graft may be the distal portion recited above.

Further provided is a stent graft is provided for deployment in the aortic arch including: a plurality of expandable stent rings arranged along a length of tubular graft material, the plurality including at least a proximal stent ring at or near a proximal end of the tubular graft material and a distal stent ring at or near a distal end of the tubular graft material, and at least one intermediate stent ring between the proximal stent ring and the distal stent ring; at least one fenestration provided in a side wall of the tubular graft material, the fenestration configured for alignment with a junction of the left subclavian artery and for deployment of a side-branch therethrough; wherein the fenestration is aligned with a lumen of an internal branch graft located within the lumen of the stent graft; wherein the internal branch graft extends from the fenestration within the lumen of the stent graft in a distal direction.

The internal branch graft may be angled within the lumen of the stent graft such that as the internal branch graft extends distally it also extends laterally from the fenestration. The internal branch graft is preferably angled by an angle in the range of 5 to 45 degrees, as measured from the central longitudinal axis of the stent graft, most preferably by an angle of about 16 degrees.

Preferably, the internal branch graft has a proximal portion having a proximal longitudinal axis and a distal portion having a distal longitudinal axis, wherein the proximal longitudinal axis of the proximal portion intersects with a longitudinal axis of the stent graft at an acute angle, and wherein the distal longitudinal axis of the distal portion intersects with a longitudinal axis of the stent graft at an acute angle, the acute angle between the distal longitudinal axis and the longitudinal axis of the stent graft being smaller than the acute angle between the proximal longitudinal axis and the longitudinal axis of the stent graft.

Preferably, a most proximal portion of the internal branch graft is generally frustoconical and a most distal portion of the internal branch graft is cylindrical. The most proximal portion of the internal branch graft may be the proximal portion recited above and the most distal portion of the internal branch graft may be the distal portion recited above.

The length of the tubular graft material forms a graft having a proximal end and a distal end. In embodiments, the device has a first stent. The first stent may be an end most stent disposed at the proximal end of the graft. The first stent may be the proximal stent ring. The device may include a second stent adjacent to and distal of the first stent. The second stent may be one of the at least one intermediate stent rings. Each of the first and second stents may include a plurality of proximal peaks and distal valleys. In embodiments, adjacent peaks and valleys of each of the first and second stents are connected by struts. Preferably, the graft covers at least a majority of each of a plurality of interstices between peaks of the first stent. A peak of the second stent may be nested between valleys of the first stent. A strut of the second stent may be shorter than a strut of the first stent.

Additionally, the device may comprise any of the optional features disclosed herein The stent graft is an implantable medical device configured for implantation into a curved lumen. In embodiments, the stent graft is an implantable medical device including a tubular graft and a first stent around the graft. In embodiments, the tubular graft has a first end, a second end, and a sidewall. The first stent may be the proximal stent ring, one of the at least one intermediate stent rings, or the distal stent ring. The first stent has a length from a first to a second end. The length of the first stent may increase in both circumferential directions from an inner curve region of the device and provide the first stent with a wedge shape. The first end of the first stent may be adjacent to the first end of the graft.

The first end of the graft may be slanted with respect to the sidewall. The first end of the graft may form an obtuse angle with respect to the sidewall at the inner curve region. The first end of the graft is the proximal end and the second end of the graft is the distal end. The inner curve region is configured to be deployed on the inside of a curve of a lumen. The lumen may be the aortic arch.

The proximal stent ring may include a plurality of stent units including first and second stent units, each stent unit comprising first and second struts connected by a proximal apex. The proximal apex of the first stent unit may be more rounded than the proximal apex of the second stent unit. The proximal end of the tubular graft material may include first and second circumferential regions, the first circumferential region having a scallop. The proximal stent ring may be disposed at the proximal end of the tubular graft material.

The plurality of stent units may include at least one scallop unit and at least one body unit, wherein each scallop unit has a proximal apex located at the scallop and each body unit has a proximal apex located in the second circumferential region. The first stent unit may be a scallop unit of the at least one scallop unit and the second stent unit may be a body unit of the at least one body unit.

The plurality of stent units may include at least one scallop unit and at least one supporting unit, where the proximal apex of each scallop unit is located at the scallop and the proximal apex of each supporting unit is located in the second circumferential region, Preferably, the first and second struts of each of the at least one scallop unit are shorter than the first and second struts of each of the at least one supporting unit. The proximal apex of each of the at least one scallop unit may be disposed proximally of a distal end of the scallop and uncovered by graft material.

The plurality of stent units may include a plurality of scallop units and at least one body unit, wherein each scallop unit has a proximal apex located at the scallop and each body unit has a proximal apex located in the second circumferential region. Additionally, the device may comprise any of the optional features of the first and second aspects, wherein reference to the stent is to be taken as reference to the proximal stent ring.

Additionally, the device may comprise any of the optional features

There is also provided an implantable medical device configured for implantation into a curved lumen, the device including a tubular graft; the graft having a first end, a second end, and a sidewall; wherein the first end of the graft is slanted with respect to the sidewall and forms an obtuse angle with respect to the sidewall at an inner curve region of the device; wherein the inner curve region is configured to be deployed on the inside of a curve of a lumen. Additionally, the device may comprise any of the optional features of the disclosure herein.

There is also provided a stent graft for deployment in the aortic arch including a plurality of expandable stent rings arranged along a length of tubular graft material having a proximal end and a distal end, the plurality including at least a proximal stent ring at the proximal end of the tubular graft material and a distal stent ring at or near the distal end of the tubular graft material, and at least one intermediate stent ring between the proximal stent ring and the distal stent ring; at least one fenestration provided in a side wall of the tubular graft material, the fenestration configured for deployment of a side-branch therethrough; wherein the fenestration is aligned with a lumen of an internal branch graft located within the lumen of the stent graft; wherein the internal branch graft extends from the fenestration within the lumen of the stent graft; wherein the at least one intermediate stent ring is a fenestration-supporting stent ring, wherein the fenestration-supporting stent ring is a zig-zag stent having a plurality of proximal apices and a plurality of distal apices, the proximal and distal apices connected to each other by a plurality of stent struts extending therebetween, wherein at least one of the distal apices is a fenestration-supporting apex; wherein at least one fenestration is provided between two struts of the fenestration-supporting stent ring, the combination of two struts and the fenestration-supporting apex of the fenestration-supporting stent ring defining two sides and the distal end of the fenestration; and wherein the fenestration has a proximal edge, the proximal edge including at least a portion that is substantially perpendicular to the longitudinal axis of the stent graft; the proximal end of the graft material including first and second circumferential regions, the first circumferential region having a scallop longitudinally aligned with the fenestration; wherein the proximal stent ring may include a plurality of stent units, each stent unit comprising first and second struts connected by a proximal apex, the stent ring comprising a plurality of distal apices, each stent unit being connected to a Neighboring stent unit by a distal apex; wherein the plurality of stent units may include at least one scallop unit and at least one supporting unit, where the proximal apex of each scallop unit is located at the scallop and the proximal apex of each supporting unit is located in the second circumferential region; wherein the first and second struts of each of the at least one scallop unit are shorter than the first and second struts of each of the at least one supporting unit.

At least a majority of each of the at least one scallop unit is preferably overlapped by graft material. In one embodiment, the proximal apices of the at least one scallop unit do not extend proximally of the graft material at the scallop. The plurality of stent units can include a plurality of scallop units. The plurality of stent units may include at least one body unit, wherein each body unit has a proximal apex located in the second circumferential region. The proximal edge of the fenestration can connect the proximal ends of the two sides of the fenestration.

A sealing stent ring may be provided adjacent the proximal edge of the fenestration. The sealing stent ring can be located distally of the proximal stent ring. The sealing stent ring can have a plurality of proximal apices and the proximal apices of the sealing stent ring can be located distally of the distal apices of the proximal stent ring, such that a region of unstented graft material is provided between the proximal stent ring and the sealing stent ring. The length of the region of unstented graft material between the proximal stent ring and the sealing stent ring can be from about 4 mm to about 10 mm, and preferably about 7 mm. Therefore, proximally of the fenestration only two stents are provided: the proximal stent ring at the proximal end of the stent graft, and the sealing stent ring provided adjacent the proximal edge of the fenestration.

The sealing stent ring can be a zig-zag stent having proximal and distal apices, and the proximal edge of the fenestration may not extend proximally of the distal apices of the sealing stent ring. Only a single fenestration may be provided in the side wall of the tubular graft material. The plurality of stent units can include at least one supporting unit having a proximal apex located in the second circumferential region with each of the at least one supporting unit supporting the scallop. The plurality of stent units can include at least one supporting unit having a proximal apex located in the second circumferential region with each of the at least one supporting units being adjacent to the scallop. Optionally the at least one supporting unit may include a supporting unit disposed on each side of the scallop. The plurality of stent units can include at least one supporting unit having a proximal apex located in the second circumferential region with the proximal apex of each of the at least one scallop unit being disposed distally of the proximal apex of each of the at least one supporting unit. The plurality of stent units may include at least one supporting unit having a proximal apex located in the second circumferential region with the proximal apex of each of the at least one supporting unit being overlapped by graft material.

The proximal apex of each of the at least one supporting unit can be disposed at a proximal edge of the graft. A plurality of the distal apices of the proximal stent ring are preferably located in the second circumferential region and are disposed longitudinally level with or distally of a distal end of the scallop. At least a majority of the distal apices of the proximal stent ring are disposed longitudinally level with or distally of the distal end of the scallop. The distal apices of the proximal stent ring can be substantially aligned with one another. In general, the first and second circumferential regions make up a complete circumference of the graft.

Features of the preceding disclosure also may be included.

There is also provided a kit including a stent graft as described above and a bridging stent graft, wherein the bridging stent graft is configured for deployment in the left subclavian artery of a patient and for engagement with the fenestration and at least a proximal end of the internal branch graft of the stent graft of the ninth aspect, wherein the bridging stent graft may include a tubular graft material having a plurality of stent rings arranged along its length, wherein the stent graft of the ninth aspect may include a sealing stent ring adjacent the proximal edge of the fenestration, wherein at least one of the stent rings of the bridging stent graft has a higher radial force than the sealing stent ring of the stent graft of one or more of the previously described sealing stent rings.

More than one of the stent rings of the bridging stent graft may have a higher radial force than the sealing stent ring of the stent graft. For example, at least two, at least three or at least four of the stent rings of the bridging stent graft may have a higher radial force than the sealing stent ring of the stent graft.

There is also provided a method comprising: inserting a device according any of the disclosure herein into the vasculature of a human; and deploying the device into the aortic arch. The method may further comprise deploying the device into the aortic arch such that a distal end of the scallop is aligned between the subclavian and carotid arteries.

There is also provided a deployment system configured to deploy the device of any preceding aspect, including: an introducer configured to deploy the device in a curved lumen; the device being mounted on the introducer such that the inner curve region is arranged to be deployed on the inside of a curve of a lumen. The introducer preferably may include a pre-curved cannula.

There is also is provided a method of deploying a device according to any preceding aspect in a curve of a lumen, optionally using the deployment system recited above, the method including deploying the device with the inner curve region on the inside of the curve of the lumen. The method may include deploying the wedge-shaped stent of the device so that the first end of the wedge-shaped stent and/or the first end of the graft deploys substantially perpendicular to the curve of the lumen. The lumen may be the aortic arch, preferably between the ascending and descending aorta.

There is also provided a method comprising: inserting a device according to any preceding aspect into the vasculature of a human; and deploying the device into the aortic arch. The method may further comprise deploying the device into the aortic arch such that the stent having one or more nested peaks is positioned between the subclavian and carotid arteries.

The invention claimed is:

1. A stent graft for deployment in an aortic arch including:

a plurality of expandable stent rings arranged along a length of tubular graft material having a proximal end and a distal end, the plurality including a proximal stent ring at the proximal end of the tubular graft material and a distal stent ring at or near the distal end of the tubular graft material, and at least one intermediate stent ring between the proximal stent ring and the distal stent ring;

at least one fenestration provided in a side wall of the tubular graft material;

an internal branch disposed within a lumen and extending from one of the at least one fenestration toward an end of the stent graft;

first and second circumferential regions at the proximal end of the tubular graft material;

a scallop in the first circumferential region and longitudinally aligned with the fenestration;

wherein one of the at least one intermediate stent ring is a fenestration-supporting stent ring, wherein the fenestration-supporting stent ring is a zig-zag stent having a plurality of proximal apices and a plurality of distal apices, the proximal and distal apices connected to each other by a plurality of stent struts extending therebetween, wherein one of the distal apices is a fenestration-supporting apex;

wherein the one of the at least one fenestration is provided between two struts of the fenestration-supporting stent ring, the combination of the two struts and the fenestration-supporting apex of the fenestration-supporting stent ring defining two sides and a distal end of the one of the at least one fenestration;

wherein the one of the at least one fenestration has a proximal edge, the proximal edge including at least a portion that is substantially perpendicular to a longitudinal axis of the stent graft;

wherein the proximal stent ring comprises a plurality of stent units, each stent unit comprising first and second struts connected by a proximal apex, the proximal stent ring comprising a plurality of distal apices, each stent unit being connected to a neighboring stent unit by one of the distal apices;

wherein the plurality of stent units includes at least one scallop unit and at least one supporting unit, where the proximal apex of each scallop unit is located at a laterally extending edge of the scallop in the first circumferential region and the proximal apex of each supporting unit is located in the second circumferential region;

wherein the first and second struts of each of the at least one scallop unit are shorter than the first and second struts of each of the at least one supporting unit.

2. The stent graft of claim 1, wherein at least a majority of each of the at least one scallop unit is overlapped by graft material.

3. The stent graft of claim 2, wherein each proximal apex of the at least one scallop unit does not extend proximally of the graft material at the scallop.

4. The stent graft of claim 3, wherein the plurality of stent units includes a plurality of scallop units.

5. The stent graft of claim 1, wherein the plurality of stent units includes at least one body unit, wherein each body unit has a proximal apex located in the second circumferential region.

6. The stent graft of claim 5, wherein a sealing stent is provided adjacent the proximal edge of the one of the at least one fenestration.

7. The stent graft of claim 6, wherein the sealing stent ring is a zig-zag stent having proximal and distal apices, and wherein the proximal edge of the one of the at least one fenestration does not extend proximally of the distal apices of the sealing stent ring.

8. The stent graft of claim 6, wherein only a single fenestration is provided in the side wall of the tubular graft material.

9. The stent graft of claim 1, wherein the at least one supporting unit comprises a first supporting unit disposed along a first longitudinally extending side of the scallop and a second supporting unit disposed along a second longitudinally extending side of the scallop.

10. The stent graft of claim 1, further comprising at least one conformance tie disposed about a circumference of the proximal stent ring.

11. The stent graft of claim 10, wherein the at least one conformance tie is disposed about a distal end of the proximal stent ring.

12. The stent graft of claim 11, wherein the at least one conformance tie is disposed about the distal apices of the proximal stent ring.

13. A stent graft for deployment in an aortic arch including:

a plurality of expandable stent rings arranged along a length of tubular graft material having a proximal end and a distal end, the plurality including a proximal stent ring at the proximal end of the tubular graft material and a distal stent ring at or near the distal end of the tubular graft material, and at least one intermediate stent ring between the proximal stent ring and the distal stent ring;

at least one fenestration provided in a side wall of the tubular graft material;

an internal branch disposed within a lumen and extending from one of the at least one fenestration toward an end of the stent graft;

first and second circumferential regions at the proximal end of the graft material;

a scallop in the first circumferential region and longitudinally aligned with the one of the at least one fenestration;

wherein one of the at least one intermediate stent ring is a fenestration-supporting stent ring, wherein the fenestration-supporting stent ring is a zig-zag stent having a plurality of proximal apices and a plurality of distal apices, the proximal and distal apices connected to each other by a plurality of stent struts extending therebetween, wherein one of the distal apices is a fenestration-supporting apex;

wherein the one of the at least one fenestration is provided between two struts of the fenestration-supporting stent ring, the combination of the two struts and the fenestration-supporting apex of the fenestration-supporting stent ring defining two sides and the distal end of the one of the at least one fenestration;

wherein the one of the at least one fenestration has a proximal edge, the proximal edge including at least a portion that is substantially perpendicular to a longitudinal axis of the stent graft;

wherein the proximal stent ring comprises a plurality of stent units, each stent unit comprising first and second struts connected by a proximal apex, the proximal stent ring comprising a plurality of distal apices, each stent unit being connected to a neighboring stent unit by one of the distal apices;

wherein the plurality of stent units includes a plurality of scallop units, a plurality of supporting units, and a plurality of body units, wherein the proximal apex of each scallop unit is located at a laterally extending edge of the scallop in the first circumferential region, the proximal apex of each supporting unit is located in the second circumferential region, and the proximal apex of each body unit is located in the second circumferential region;

wherein the proximal apices of each scallop unit do not extend proximally of the graft material of the scallop;

wherein the first and second struts of each scallop unit are shorter than the first and second struts of each supporting unit.

14. The stent graft of claim 13, further comprising at least one conformance tie disposed about a circumference of the proximal stent ring.

15. The stent graft of claim 14, wherein the at least one conformance tie is disposed about a distal end of the proximal stent ring.

16. The stent graft of claim 15, wherein the at least one conformance tie is disposed about the distal apices of the proximal stent ring.

17. The stent graft of claim 16, wherein the at least one conformance tie passes a set of distal apices of the proximal stent ring and weaves through the graft material at those distal apices.

18. The stent graft of claim 13, wherein the proximal apices of each scallop unit do not extend proximally of the graft material of the scallop.

19. A stent graft for deployment in an aortic arch including:

a plurality of expandable stent rings arranged along a length of tubular graft material having a proximal end and a distal end, the plurality including a proximal stent ring at the proximal end of the tubular graft material and a distal stent ring at or near the distal end of the tubular graft material, and at least one intermediate stent ring between the proximal stent ring and the distal stent ring;

at least one fenestration provided in a side wall of the tubular graft material;

an internal branch disposed within a lumen and extending from one of the at least one fenestration toward an end of the stent graft;

first and second circumferential regions at the proximal end of the graft material;

a scallop in the first circumferential region and longitudinally aligned with the one of the at least one fenestration;

at least one conformance tie disposed at least partially circumferentially about a distal end of the proximal stent ring and configured to constrict a diameter of the proximal stent ring;

wherein one of the at least one intermediate stent ring is a fenestration-supporting stent ring, wherein the fenestration-supporting stent ring is a zig-zag stent having a plurality of proximal apices and a plurality of distal apices, the proximal and distal apices connected to each other by a plurality of stent struts extending therebetween, wherein one of the distal apices is a fenestration-supporting apex;

wherein the one of the at least one fenestration is provided between two struts of the fenestration-supporting stent ring, the combination of the two struts and the fenestration-supporting apex of the fenestration-supporting stent ring defining two sides and a distal end of the one of the at least one fenestration;

wherein the one of the at least one fenestration has a proximal edge, the proximal edge including at least a portion that is substantially perpendicular to a longitudinal axis of the stent graft;

wherein the proximal stent ring comprises a plurality of stent units, each stent unit comprising first and second struts connected by a proximal apex, the proximal stent ring comprising a plurality of distal apices, each stent unit being connected to a neighboring stent unit by one of the distal apices;

wherein the plurality of stent units includes a plurality of scallop units, a plurality of supporting units, and a plurality of body units, wherein the proximal apex of each scallop unit is located at a laterally extending edge of the scallop in the first circumferential region, the proximal apex of each supporting unit is located in the second circumferential region, and the proximal apex of each body unit is located in the second circumferential region;

wherein the proximal apices of each scallop unit do not extend proximally of the graft material of the scallop;

wherein the first and second struts of each scallop unit are shorter than the first and second struts of each supporting unit.

20. The stent graft of claim 19, wherein the at least one conformance tie passes a set of distal apices of the proximal stent ring and weaves through the graft material at those distal apices.

* * * * *